(12) United States Patent
Weusthuis et al.

(10) Patent No.: US 10,190,139 B2
(45) Date of Patent: *Jan. 29, 2019

(54) **METHOD FOR LACTIC ACID PRODUCTION USING *MONASCUS* STRAINS MODIFIED FOR LACTIC ACID PRODUCTION**

(71) Applicant: TOTAL RESEARCH & TECHNOLOGY FELUY, Seneffe (Feluy) (BE)

(72) Inventors: Alexander Ruud Weusthuis, GD Heelsum (NL); Emil Johan Harald Wolbert, LP Wageningen (NL); Jan Springer, AL Wageningen (NL); John Van Der Oost, HZ Renkum (NL); Gerrit Eggink, SC Ede (NL)

(73) Assignee: Total Research & Technology Feluy S.A., Seneffe (Feluy) (BE)

(*) Notice: Subject to any disclaimer, the term of this patent is extended or adjusted under 35 U.S.C. 154(b) by 0 days.

This patent is subject to a terminal disclaimer.

(21) Appl. No.: 15/718,153

(22) Filed: Sep. 28, 2017

(65) Prior Publication Data

US 2018/0119179 A1 May 3, 2018

Related U.S. Application Data

(62) Division of application No. 13/882,460, filed as application No. PCT/EP2011/068968 on Oct. 28, 2011, now Pat. No. 9,809,831.

(60) Provisional application No. 61/407,747, filed on Oct. 28, 2010.

(30) Foreign Application Priority Data

Oct. 28, 2010 (EP) .................................... 10290583

(51) Int. Cl.
| | |
|---|---|
| *C12P 7/40* | (2006.01) |
| *C12P 7/46* | (2006.01) |
| *C12P 7/62* | (2006.01) |
| *C12N 9/04* | (2006.01) |
| *C12P 7/56* | (2006.01) |
| *C12R 1/645* | (2006.01) |

(52) U.S. Cl.
CPC .............. *C12P 7/40* (2013.01); *C12N 9/0006* (2013.01); *C12P 7/46* (2013.01); *C12P 7/56* (2013.01); *C12P 7/625* (2013.01); *C12R 1/645* (2013.01); *C12Y 101/01027* (2013.01)

(58) Field of Classification Search
None
See application file for complete search history.

(56) References Cited

U.S. PATENT DOCUMENTS

| | | | |
|---|---|---|---|
| 5,332,839 A | 7/1994 | Benecke et al. | |
| 6,320,077 B1 | 11/2001 | Eyal et al. | |
| 8,900,834 B2* | 12/2014 | Weusthuis | C12N 9/0006 435/135 |
| 9,777,298 B2* | 10/2017 | Weusthuis | C12N 9/0006 |
| 2005/0214915 A1 | 9/2005 | Saito et al. | |
| 2007/0131010 A1 | 6/2007 | Binder et al. | |
| 2010/0009419 A1 | 1/2010 | Burk et al. | |
| 2010/0159542 A1 | 6/2010 | Scholten et al. | |
| 2011/0081694 A1 | 4/2011 | Verwaal et al. | |
| 2011/0143409 A1 | 6/2011 | Seo et al. | |
| 2011/0155557 A1 | 6/2011 | Coszch et al. | |
| 2012/0005788 A1* | 1/2012 | Richard | C12N 9/0006 800/297 |
| 2012/0122169 A1 | 5/2012 | Voelker et al. | |

FOREIGN PATENT DOCUMENTS

| | | |
|---|---|---|
| EP | 1 325 959 | 7/2003 |
| WO | 2007/032792 | 8/1988 |
| WO | 2010/118932 | 10/2010 |

OTHER PUBLICATIONS

Hsu et al., "Addition of Autotrophic Carbon Fixation Pathways to Increase the Theoretical Heterotrophic Yield of Acetate", The Fourth International Conference on Computational Systems Biology (ISB2010), Suzhou, China, Sep. 9-11, 2010, pp. 314-322.*
Prather et al. Curr Opin Biotechnol. Oct. 2008;19(5):468-74.*
Qin, Hanzhang, Chapter 1, Application of Micro-organism in the Manufacture of Chinese Spirits, Science and Technology of Chinese Spirits' Brewage, China Light Industry Press, pp. 90-91 (1997).
Ding, Hongmei, Journal of Zhejiang Chinese Medical University, vol. 32, pp. 247-248 (2008).
Hummel et al., Acidity and Lactonization of Xylonic Acid: A Nuclear Magnetic Resonance Study, J. Carbon Chem., vol. 29, pp. 416-428 (2010).
Panda et al., Production of Angkak through Co-culture of Monascus Purpureus and Monascus Ruber, Brazil J. Microbiol., vol. 41, pp. 757-764 (2010).
Tseng et al., Growth, Pigment Production and Protease Activity of Monascus Purpureus as Affected by Salt, Sodium Nitrite, Polyphosphate, and Various Sugars, J. Appl. Microbiol., vol. 88, pp. 31-37 (2000).
Madhavan et al., An Overview of the Recent Developments in Polylactide (PLA) Research, Bioresource Technology, vol. 101, No. 22, pp. 8493-8501 (2010).
Gao et al., Separation of 1,3-propanediol from glycerol-based fermentations of Klebsiella by alcohol precipitation and dilution crystallization, Front. Chem. Eng. China, vol. 1, pp. 202-207 (2010).
Williams et al., A highly active zinc catalyst for the controlled polymerization of lactide, J. Am. Chem. Soc., vol. 125, pp. 11350-11359 (2003).
Yang et al., Agrobacterium tumefaciens-mediated transformation of Monascus ruber, J. Microbicol. Biotechnol., vol. 18, pp. 754-758 (2008).

(Continued)

*Primary Examiner* — Christian L Fronda
(74) *Attorney, Agent, or Firm* — David Kelly; Gene J. Yao; Barnes & Thornburg LLP

(57) ABSTRACT

Tools and methods for producing organic acids using strains of *Monascus* which are tolerant to high organic acid concentrations at low pH.

9 Claims, 28 Drawing Sheets

Specification includes a Sequence Listing.

(56) References Cited

OTHER PUBLICATIONS

Third Office Action, Chinese Patent Application No. 201180063627.6.
Second Office Action, Chinese Patent Application No. 201180063627.6.
Panagou, et al. "Use of Gradient Plates to Study Combined Effects of Temperature, pH, and NaCl Concentration on Growth of Monascus ruber van Tieghem, an Ascomycetes Fungus Isolated from Green Table Olives"; Applied and Environmental Microbiology, vol. 71, No. 1, (2005), pp. 392-399.
Yanchun, et al. "Characteristic Analysis of Transformants in T-DNA Mutation Library of Monascus ruber"; World Journal of Microbiology and Biotechnology, vol. 25, No. 6, (2009), pp. 989-995.
Yan-Chun, et al.; "The Targeted-deletion Technology in the Monascus ruber Mediated via Agrobacterium tumefaciens"; (2009), pp. 1-1 Retrieved from http://en.cnki.com.cn/Article_en/CJFDTOTAL-WSWT200902023.htm.
Hassan, et al. "Kinetic Analysis of red pigment and and citrinin production by Monascus ruber as a function of organic acid accumulation"; Enzyme and Microbial Technology, vol. 27, No. 8, (2000), pp. 619-662.
Singh, et al. "Metabolic Engineering Approaches for Lactic Acid Production"; Process Biochemistry, Elsevier, NL, vol. 41, No. 5, (2006), pp. 991-1000.
International Search Report for PCT/EP2011/068968 dated Feb. 2, 2012.
Chica et al. Curr. Opin Biotechnol. Aug. 2005:16(4)378-84.
Sen et al. Appl Biochem Biotechnol. Dec. 2007:143(3):212-23.
Hsu et al., "Addition of Autotrophic Carbon Fixation Pathways to Increase the Theoretical Heterotrophic Yield of Acetat", The Fourth International Conference on Computational Systems Biology (ISB2010), Suzhou, China, Sep. 9-11, 2010, pp. 314-322.
Database EMBL, "Monascus purpureus strain CICC5031 pyruvate decarboxylase mRNA, complete CDS," Jun. 9, 2010.
Office Action dated Mar. 27, 2017 in corresponding Chinese Application No. 201180063627.6.

* cited by examiner

Codon optimized Bt-L-LDH gene (Seq ID 1.)

ATGGCAACCCTGAAGGACCAGCTTATCCAAAACCTGCTCAAGG
AAGAACACGTCCCCCAAAACAAGATTACTATCGTCGGAGTCGG
TGCCGTTGGAATGGCCTGCGCTATCTCCATTCTGATGAAGGAC
CTCGCAGATGAGGTGGCGCTCGTCGACGTTATGGAGGATAAGC
TCAAGGGTGAAATGATGGACCTTCAGCATGGATCGCTTTTCTT
GCGCACACCCAAGATCGTCAGCGGCAAGGATTACAACGTTAC
AGCAAATTCCCGCCTTGTGATCATTACTGCAGGCGCGCGTCAG
CAAGAGGGTGAATCGAGACTGAACCTCGTCCAAAGGAACGTT
AATATCTTCAAGTTCATCATCCCCAACATTGTCAAGTACTCCCC
AAATTGTAAGCTGCTCGTCGTTTCTAATCCGGTTGACATCCTCA
CTTATGTGGCCTGGAAGATTTCTGGCTTCCCTAAGAACCGAGTT
ATCGGCTCGGGTTGCAATCTTGATAGCGCTCGATTTCGGTATCT
TATGGGAGAGAGATTGGGCGTCCATCCCCTGTCCTGTCACGGC
TGGATCTTGGGAGAACACGGCGACTCCTCTGTGCCAGTCTGGT
CGGGTGTCAACGTGGCCGGAGTCAGCCTTAAGAATTTGCATCC
GGAGTTGGGCACCGACGCCGATAAGGAACAGTGGAAGGCTGT
CCACAAGCAAGTGGTCGACTCCGCATACGAGGTTATCAAGCTG
AAGGGATATACCTCCTGGGCGATTGGCCTCTCTGTGGCCGATC
TTGCTGAAAGCATCATGAAGAACTTGCGCCGTGTCCATCCTAT
CTCCACGATGATTAAGGGTCTGTACGGAATTAAGGAAGACGTG
TTTTTGTCTGTCCCCTGCATCCTGGGCCAGAATGGTATTTCGGA
TGTTGTGAAGGTCACCCTCACGCACGAGGAAGAGGCTTGCTTG
AAGAAGTCGGCGGACACTCTCTGGGGCATCCAAAAGGAACTC
CAATTTTAA

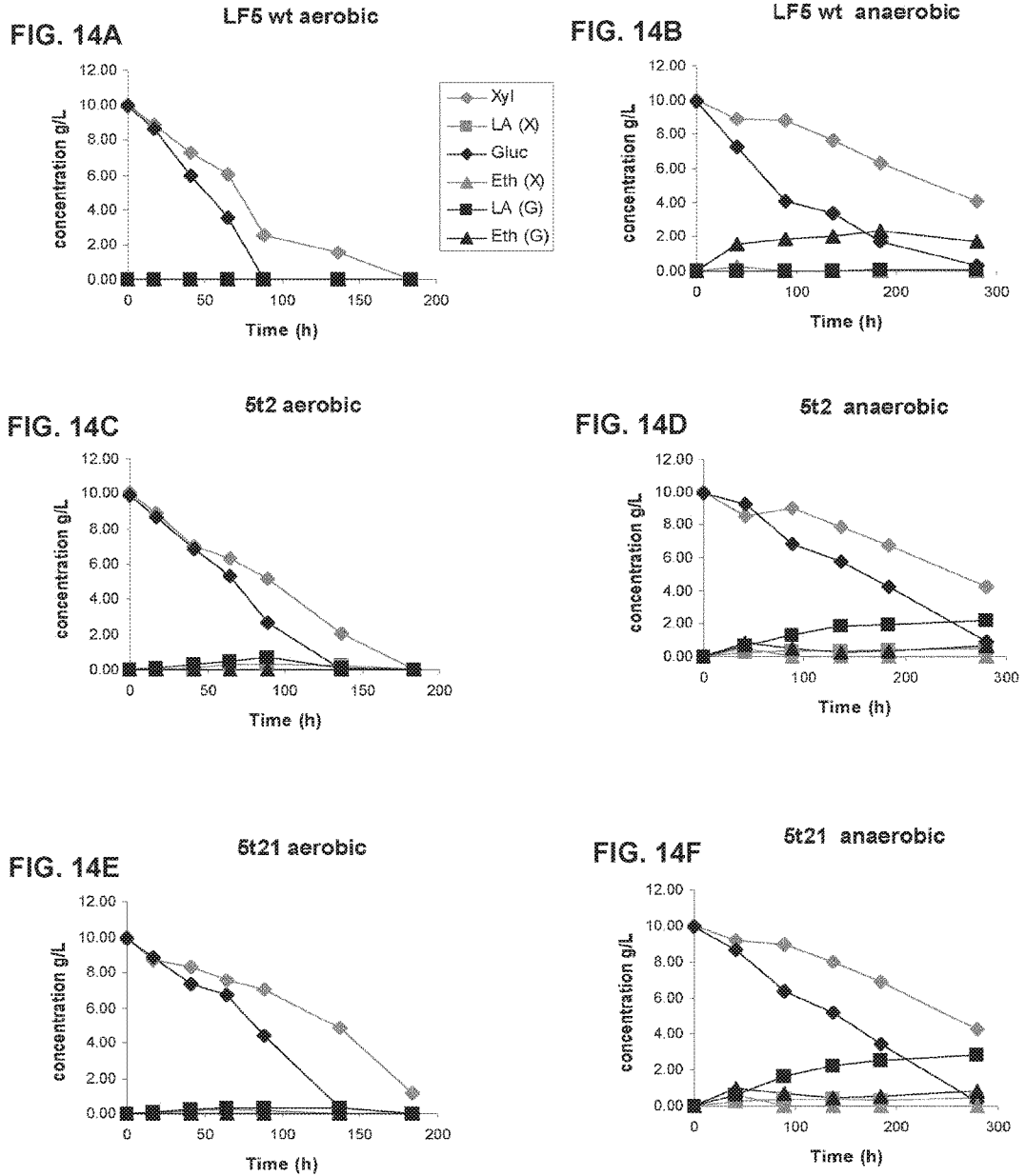

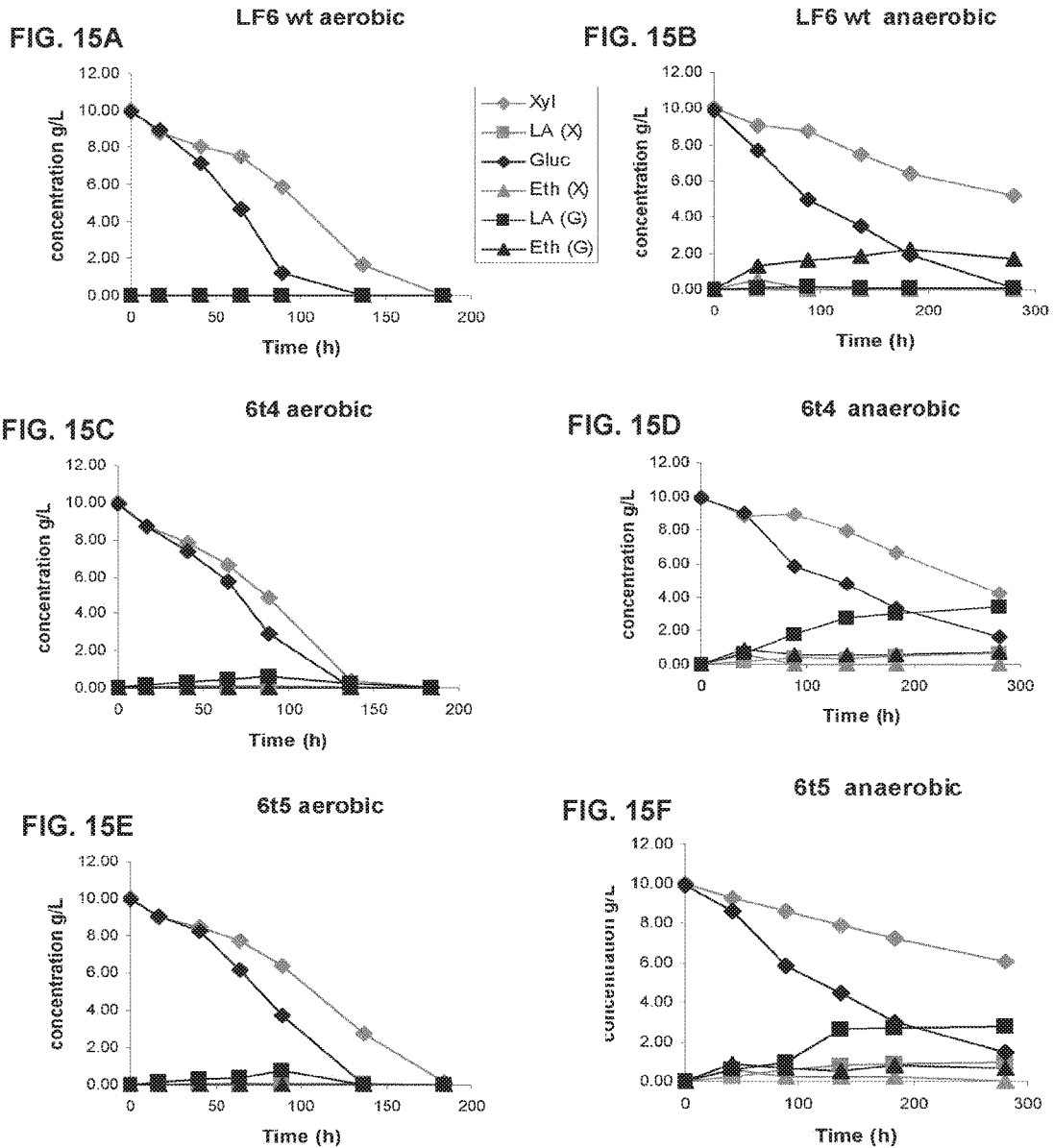

Monascus ruber PDC1 open reading frame (Seq ID NO:3)

TGGGTGGGYAAYTGYAATGARCTGAATGCTGGTTACKCCGCCG
ATGGCTACGCTCGTATCAAGGGTATCTCTGCCCTGATCACCACT
TTCGGTGTCGGTGAGCTCTCTGCCGCCAACGCCATCGCCGGTT
CCTACTCGGARCGGGTGCCCGTTGTCCACATTGTCGGTGAGCC
CAGCACGGCATCCCAGAACAACCGCCAGCTTCTGCACCACACC
CTCGGAAACGGTGACTTCGATGTCTTCGAGAAGATCTTCGCCA
AGATCTCTACTTCCGTCGTTAAGATTAGAGACCCCGCCAATGC
CGCCACCATGATCGACCACGTTCTCCGGGAATGTGTTATCCAG
AGCCGCCCCGTCTACATCGGTCTGCCCTCTGATATGGTTACCA
AGAAGGTTGAGGGAGCCCGCCTGAAGACCCCCATCGACCTGTC
CCTCCCCGAGAACCCCAAGGAGAAGGAGGACTACGTCGTCAG
CGTCGTTCTCAAGTATCTGCACGCTGCCAAGAACCCTGTCATC
CTCGTCGATGCCGGTGTCAACCGCCACAATGCCCAGGCTGAGG
TGCACGAGCTGATCAAGAAGTCTGGAATCCCCACCTTCATCAC
CCCCATGGGCAAGGGCGGTGTTGACGAAACCCTCCCCAACTAC
GGCGGTGTCTACGCCGGTACCGGTTCCAACAGGGGCGTCCGCG
AGCGTGTCGAGGAATCTGACCTCATCCTGAACATCGGACCTCT
CCAGTCCGACTTCAACACCACCGGCTTCTCCTACCGCACCAGC
CAGCTCAACACCATCGAGTTCGACCGCGACAGCGTCCAGGTCC
GCTACTCCTACTACCCCGACATCCAGCTTAAGGGAGTTCTCCA
GAACCTCATCGCCACCATGGGCGAACTCAACATCGAGCCTGGC
CCGACCCCCTCCAACGCCCTCCCCGCCAACGGCGTTGACCACG
AAACTGCAGAGATCACCCACGAATGGCTCTGGCCCATGGTCGG
CAACTGGCTCCGCGAAGGTGATGTTGTCCTCACTGAAACCGGT
ACCGCCAACTTCGGTATCTGGGAAACCCGCTTCCCCAAGAACG
TTCAGGCCATCTCCCAGGTCCTCTGGGGTTCCATCGGTTACTCC
GTCGGTGCCTGCTTGGGTGCTGCTCTCGCCGCTCGGGAACTTG
GCGACAACCGTGTCCTACTCTTCGTCGGTGATGGTAGCTTYCA
GATGACCGCCCAGGAGATCAGCACTATGATCCGTCAGGGATTG
AAGCCTATTGTCTTCGTCATCTGCAACAACGGCTACACMATCG
ARMGCTACATCCACGG

FIG. 16

Monascus ruber PDC2 open reading frame (SEQ ID NO: 4)

CTGAACGCCGSCTACGCCGCCGACGGATAYGCTCGTGTCAATG
GAATCGCTGCCTTGGTTACTACTTTCGGTGTAGGAGAGCTGTC
AGCAGTGAACGCCATTGCGGGAGCCTACTCAGAGTATGTACCC
ATCGTTCACATTGTTGGCCAACCAAATACAAGGTCACAGAGAG
ATGGAATGCTGTTGCATCATACGTTGGGCAACGGCGACTTTGA
TGTCTTTACCAAGATGAGTGCTTCCATTTCGTGCGCTGTTGCAA
AGTTGAACGACCCCATGAAGCTGCAACGCTCATCGACCACGC
CATTCGGGAATGCTGGATTCGCAGCAGACCGGTGTACATCACC
CTCCCTACAGACATCGTCACGAAGAAAGTCGAAGGTGAAAGG
CTGAAGACCCCAATTGACCTGACAATGCCAGAGAATGAAGCA
GAAAGGGAAGATTACGTGGTGGATGTTGTTTTGAAATACCTGC
AAGCCGCGAAAAACCCAGTCATTCTAGTTGACGCATGCGCAAT
CCGTCACAGGGTCCTGGACGAGGTACATGACCTTGTTAAGGCT
TCTGGCTTGCCAACCTTTGTGACCCCAATGGGCAAAGGAGCAG
TGGACGAGACTCATCCAAATTATGGTGGTGTGTATGCTGGAGA
TGGGTCTAATACCGGCGTCCGTGAAGTTGTTGAAGCTTCCGAC
CTTATTCTGAGCATTGGCGCCATTAAATCCGATTTCAATACTGC
CGGCTTCACATACCGCATCGGCCAACTTAACACGATCGACTTC
CATAGTACCTTCGTGCGAGTGAGGTATTCGGAGTACCCGAACA
CAAACATGAAGGGTGTTCTAAGGAAGATCATCCAGAAAATGG
GCCCCCTCAGCAAGACGCCTATTCCAAAGACTATCAACAAGGT
TCCAGAACATATCAAAGCTTCTGGTGACACGCGGATTACTCAT
GCTTGGTTGTGGCCGACAGTCGGACAGTGGCTGCAGCCGGAGG
ATGTTGTCGTCACTGAGACTGGAACTGCAAACTTTGGAATCTG
GGAAACCAGGTTCCCACACGGTGTCACGGCTATAAGCCAAGTC
CTCTGGGGAAGCATTGGGTACACGGTTGGAGCATGTCAAGGCG
CCGCACTAGCTGCAAAGGAGATAGGCAACCGTCGCACTGTACT
TTTTGTTGGCGATGGCAGTTCCAGCTTACCGCGCAGGAAGTG
AGCACCATGCTCAGAAATAAGCTGAACCCGATCATTTTTGTGA
TCTGTAACGAAGGGTAYACRATCGAGCGCTACATCCATGGC

FIG. 17

Monascus rubber gene encoding PDC4 (SEQ ID No: 5)

ATGACCACTGTCGGAAGCTACCTCGCAGAAAGGCTCTCCCAAATTGGCATCGAGCGC
CACTTCGTCGTCCCAGGCGACTACAACCTCATCCTCCTCGACAAACTCCAACAACAC
CCCAAACTCGACGAAATCAACTGCACAAATGAACTAAACTGCTCCATGGCCGCAGAA
GGCTACGCCCGCGCAAAAGGCGTAGCCGCCTGCGTCGTGACGTTCAGCGTCGGCGCA
TTCTCCGCATTCAACGGCATCGGCAGCGCATACGGTGAGAATCTCCCTGTCATCCTC
ATCTCCGGTTCCCCTAATACCAACGATCTTGGCTCGTCGCATTTGCTGCATCATACG
ATCGGTACGCATAATTTTGACTACCAGCTTGAGATGGCGAAAAATATCACCTGCTGT
GCTGTTGCGATTCGTCGTGCCTCGGATGCGCCGCGGTTGATCGACGAGGCTATTCGC
ACCGCACTTCGGGCGCGGAAACCAGCGTATATTGAGATTCCTACGAACCTCTCGGGC
CAGCCGTGTTCCCTGCCCGGACCGGCGTCGGGATTCTCAAGCCGGATACGAGTGAT
ATTGATACTCTTGCGGAAGCGCTGAAGGCAGCCAACGACTTCCTCTACCCGGAAC
AAGGTGTCCTTACTGGTTGGCCCTAAGGTTCGCGCAGCAGGCGCTGAACATGCCGTG
ATCCATCTTGCTCAAGCCCTGGGATGCGCGGTGGCCGTGCTACCCAGTGCCAAATCG
TTCTTCCCGGAGACTCATCCGCAGTTCGTGGGTGTATACTGGGGCGAAGTGAGCACG
AAGGGCGCGAATGCTATCGTCGACTGGTCCGATACCCTTATTTGCGTGGGGACGGTT
TACACCGACTACAGCACCGTTGGATGGACGGGGCTACCCGAAGCAGCCAGTCTGACC
ATTGACCTGGACCATGTCAGTTTCCCTGGATCCGATTACAACCAGATCCATATGCTG
GAGTTCGTGGCAGGACTGGCGAAGCTGGTGAAGAAGAACCCCCTGACACTCGTCGAA
TATAACCGTCTGCAACCAGACCCTCTCGTTCACACGCCATCTCCGCCGGATCAACGA
CTGAGCCGGCGAGAAATGCAGTACCAGATCAGCCAGTTCCTGACGCGCAACACGACG
GTCGTTGTGGACACGGGCGACTCGTGGTTCAACGGGATGCAGATGGACCTTCCGGAC
GGAGTGAGATTTGAGGTTGAGATGCAATGGGGACACATCGGATGGTCCGTTCCAGCA
GCACTGGGTCTGGCCGCCGCAAACCCCGAGCGACAGATAGTCGTCATGGTAGGCGAT
GGGTCGTTCCAGATGACGGGCCACGAGGTGTCAAATATGACTCGATTAGGGCTACCG
ATTATCATCTTCCTGATCAACAATGACGGGTACACAATCGAAGTCGAGATCCACGAT
GGCATCTACAACAACATCAAGAACTGGGATTACGGCGCGTTCGTCGAGTCGTTCAATGCCAAGGAG
GGACATGGGAAGGGGTATCGTGTTACCACGGCGGGGAAATGCACAGGGCCATTGAGGCGGCGAAGAAG
AATAAACAGGGGCCAACACTAATCGAGTGTGATATTGATCGCGATGATTGCAGTAAGGAGTTGATCAGT
TGGGGGCATTATGTGGCTGCTGCGAATGGCAAGCCTCCTGTTGCCAGGTGA

FIG. 24

Monascus ruber CYB2 open reading frame (SEQ ID NO: 2)

AAGTATGCGGGGCAGGATGCCACAAAGGCCTATTCTGAAGTTC
ACACTCCGAGCCTTATCAAATGGAATTTATCCCCAGACAAGCT
CAAGGGCACTCTCGGCCAATCCACTATTGACGATGAATGGATG
AAACCACCGCCAAATGAGAGCGACAAAGTTGTTTTAGAGAAC
GAGAAACCGCCGCTGCATATGCTGATAAACTCGCACGATTTCG
AAGTCGTAGCTTCCAAGACTGCAAGTAAGAAGACCTGGGCCTT
CTATTCCAGCGCTGCAACGGACCTCATCACCCGTGATGCCAAT
AAGTCATGCTTTGACCGGATATGGTTCCGACCCCGGGTACTGA
GGAATGTGCGTACCGTCAAAACGCGCACGAAGATCCTCGGGGT
TGACAGCAGTCTCCCACTTTCGTGAGTCCAGCAGCTATGGCT
AAGCTCATTCACCCAGATGGTGAGTGTGCCATAGCAAGGGCAT
GTGCAAATAAGGGTATCATTCAAGGTGTACgttcattgcagattcgaacactt
cccgttctagttgcaaccttcttaacatcaatgtcggatagGTGTCGAATAACTCATCAT
TCCCAATCGAAGAGCTCCGGGAGGCGGCACCGTCTGGAAATTT
TATTTCCAGTTATATGTGAATCGGGATCGAGAGAAATCTGCG
GAACTACCGCAGGTGCTCAGCTAACCCGAACATCAAGGCCA
TCTTCGTGACCGTTGACGCAGCCTGGCCCGGTAAACGTGAGGC
AGACGAACGAGTCAAAGCGGATGAGAGCCTGACAGTCCCCAT
GTCCCCATCGACAACACGCAACGACAAAAGGGGGGCGGGCT
CGGGCGCGTTATGGCTGGGTTCATCGACCCGGGGCTCACCTGG
GAAGATCTGGCCTGGGTGCGACAACATACCCATCTCCCCGTTT
GTCTGAAGGGAATTATGTCCGCAGACGATGCCATTCTAGCCAT
GAAATTGGGACTAGATGGCATCCTGCTCTGCAACCACGGCGGC
CG

FIG. 26

Gene Mona00569 encoding cytochrome dependent L-LDH (SEQ ID No: 6)

| | | | |
|---|---|---|---|
| ATGTCTCAAC | CTAAGCTTAC | CGGCGCTGAT | ATCGCCAAAC |
| ACAATTCCAA | GGACTCGTGC | TGGGTCATTG | TCCACGGGAA |
| AGCATACGAT | GTCACGGACT | TCCTGCCAGG | TATTGATTGA |
| CCCCCCTGTC | CGGGAATTCC | GAGATGCTGC | CTGCGTTCAT |
| TGAATACTGA | TTTGCATGAA | TTTGATCAAT | TATAGAACAT |
| CCCGGTGGCC | AGAAGATTAT | CCTGAAGTAT | GCCGGCAGAG |
| ATGCCACGGA | AGAATTCGAG | CCCATCCACC | CCCCGGATAC |
| CCTGGACAAG | TACCTCGACA | AGTCAAAGCA | CTTGGGCGAG |
| GTCGACATGG | CCACTGTCGC | ACACGACGAG | AAGGCTGTCG |
| ATCCCGAGGA | GACGGCTCGC | CAGGAAAGAA | TCAAGCTCAT |
| GCCATCGTTG | CAATCCTGCT | ACAATCTGAT | GGACTTTGAA |
| TCCGTGGCGC | AGCAGGTCAT | GAAGAAGACT | GCGTGGGCAT |
| ACTACTCAAG | TGGTGCTGAT | GATGAAATCG | TATGACCATA |
| TCTGGATTTC | TCGTTCCCTT | TGCAGCACAT | ACTGACTTGC |
| GTCTGTTCAC | AGACCCTGCG | AGAAAACCAC | ACTGCCTTCC |
| ATAAGATCTG | GTTCCGGCCG | CGAGTCCTAG | TCGACGTGGA |
| ACATGTCGAC | TACTCTACGA | CCATGCTGGG | AACCAAGGTC |
| TCCGCTCCCT | TCTATGTGAC | GGCCACAGCC | CTGGGCAAAC |
| TGGGACACCC | CGAGGGTGAG | GTCGTTCTCA | CCCGTTCCTC |
| CTACCGTCAC | AACGTCATCC | AGATGATTCC | CACGCTCGCC |
| TCGTGCTCCT | TTGACGAGAT | TATTGACGCC | CGCCAAGGCG |
| ATCAGGTCCA | GTGGCTGCAG | CTCTACGTCA | ACAAGAACCG |
| CGATATCACC | AAGCGCATTG | TGCAACATGC | CGAAGCCCGC |

FIG. 27A

| | | | |
|---|---|---|---|
| GGCTGCAAGG | GCCTCTTCAT | CACCGTCGAC | GCCCCGCAAT |
| TAGGTCGTCG | AGAGAAAGAC | ATGCGCTCCA | AGTTCTCCGA |
| CGAGGGCTCC | AACGTCCAGA | AAGAAGAGGG | TGAGGAGAAC |
| GTCGACCGCT | CTCAGGGTGC | CGCCCGTGCT | ATCTCCTCGT |
| TCATCGACCC | CGCCCTCTCC | TGGAAGGATA | TCCCCTGGTT |
| CCAATCCATC | ACGAAGATGC | CCATCGTCCT | GAAGGGTGTG |
| CAGTGCGTCG | AAGACGTTTT | CCGTGCTATC | GAAGCCGGAG |
| TCCAGGGTGT | TGTGCTGTCC | AATCACGGTG | GCCGTCAGCT |
| CGAGTTCGCA | CCATCGGCTG | TCGAGCTTCT | GGCCGAGGTT |
| ATGCCTGCGC | TGCGCCAGCG | CGGCTTGGAG | AACAGCATCG |
| AGGTGTACAT | CGACGGTGGC | ATCCGCAGAG | GCACTGATAT |
| CGTCAAGGCG | CTCTGCCTTG | GCGCCAGGG | CGTGGGGATT |
| GGTCGTCCTT | TCCTGTACGC | CATGTCGGCG | TACGGCCAGG |
| CCGGTGTCGA | CAAGGCCATG | CAGCTTCTCA | AGGATGAGAT |
| GGAGATGAAC | ATGAGACTCA | TCGGAGCCAC | TAAGGTCTCC |
| GAGCTGAGCC | CCAGCCTCGT | CGATACCCGC | GGTCTTCTTG |
| GTGGTCACCA | CGCTCCTGTT | CCGTCCGACA | CGCTGGGCAT |
| GAAGGCGTAC | GATGCGCTCC | AGGCTCCGCG | GTTCAACGAA |
| AAGTCGAAGT | TGTAG | | |

FIG. 27B

METHOD FOR LACTIC ACID PRODUCTION USING *MONASCUS* STRAINS MODIFIED FOR LACTIC ACID PRODUCTION

This application is a division of U.S. application Ser. No. 13/882,460, filed Jul. 29, 2013, which is a national stage of International Patent Application No. PCT/EP2011/068968, filed Oct. 28, 2011, which claims the priority of U.S. provisional Application No. 61/407,747, filed Oct. 28, 2010, the contents of each are hereby incorporated in their entireties

TECHNICAL FIELD

The present invention relates to microorganisms for use in organic acid production and their applications.

BACKGROUND

Organic acids are widely used in food, pharmaceutical and textile industries, and are widely recognized to be one of the key chemical building blocks in biorefining. Organic acids are also of interest for the production of polymers which are used as biodegradable plastics.

A number of microbes are capable of producing organic acids by aerobic and anaerobic fermentation processes. *Lactobacillus* species are currently used extensively in industry for starch-based lactic acid production. The majority of these species lack the ability to ferment pentose sugars such as xylose and arabinose. Although *Lactobacillus pentosus, Lactobacillus brevis* and *Lactococcus lactis* are able to ferment pentoses to lactic acid, pentoses are metabolized using the phosphoketolase pathway which is inefficient for lactic acid production. Indeed, in the phosphoketolase pathway, xylulose 5-phosphate is cleaved to glyceraldehyde 3-phosphate and acetyl-phosphate. With this pathway, the maximum theoretical yield of lactic acid is limited to one per pentose (0.6 g lactic acid per g xylose) due to the loss of two carbons to acetic acid.

In most platform host organisms such as *E. coli*, production of organic acids at high titers is either inefficient or toxic. The production of organic acids such as lactic acid at neutral pH typically results in the production of Ca-lactate, which has to be converted into lactic acid by the addition of sulphuric acid, resulting in the formation of $CaSO_4$ (gypsum) as by product. To produce lactic acid directly, the fermentation must be executed at low pH (preferably at least one unit lower than the pKa value of lactic acid, 3.85). Lactic acid however is toxic to microorganisms, as in its protonated form it acts as an uncoupler that destroys the membrane potential. Thus, while quite some micro-organisms may be tolerant to low pH only a limited number of organisms are suitable for organic acid production in that they are tolerant to organic acids at reduced pH.

An important drawback to bacterial fermentation is the cost. As many bacteria are unable to synthesize some of the amino acids or proteins they need for growing and for metabolizing sugars efficiently, bacteria often must be fed a somewhat complex package of nutrients, increasing the direct expense to operate the fermentation. In addition, the increased complexity of the broth makes it more difficult to recover the fermentation product in reasonably pure form, so increased operating and capital costs are incurred to recover the product. Also, the use of corn as the feedstock competes directly with the food and feed.

Accordingly, there remains a need for improved biocatalysts for lactic acid fermentation processes.

SUMMARY OF THE INVENTION

The present invention provides improved micro-organisms for use in organic acid production. More particularly the invention provides micro-organisms which are highly tolerant to high concentrations of organic acid at low pH and thus suitable for use in organic acid production by genetic engineering. In further particular embodiments the invention provides recombinant fungi, more particularly of a species within the *Monascus* genus wherein certain exogenous and/or endogenous genes are over-expressed and/or suppressed so that the recombinant strains produce increased levels of organic acid when cultivated in a fermentable medium. Accordingly, the recombinant *Monascus* strains of the present invention can be used for enhanced production of organic acid at low pH thereby providing an increased supply of organic acid for use in food and industrial applications.

In a first aspect, the present invention thus provides micro-organisms, more particularly of the genus *Monascus*, which are tolerant to high concentrations of organic acid at low pH. In particular embodiments they are tolerant to increased concentrations of organic acid at a pH which is less than 1.5 units above the pKa value of the organic acid. More particularly the micro-organisms of the invention are tolerant to organic acids such as lactic acid at a pH of less than 5, more particularly less than 4, even more particularly less than 3, most particularly less than 2.8. In further particular embodiments, they are capable of growing in medium containing organic acid at 50 g/L, most particularly 100 g/L, and in particular embodiments grow in medium containing organic acid of up to 150 to 175 g/L, at low pH, more particularly at a pH of less than 5 more particularly less than 4, even more particularly less than 3, most particularly less than 2.8. In particular embodiments of the invention, the species within the *Monascus* genus is *Monascus ruber*. This high acid tolerance makes them particularly suitable for use in the industrial production of organic acids, even under anaerobic or quasi-anaerobic conditions.

In particular embodiments, these micro-organisms are modified by genetic engineering to further enhance organic acid production. In particular embodiments, the micro-organisms of the invention are capable of growing on hexose and pentose sugars and convert these sugars in organic acids. In more particular embodiments the micro-organisms of the invention grow on glucose and xylose at a concentration at least 50 g/L, more particularly at concentrations of at least 70 g/L, at least 100 g/L, at least 200 g/L or more. In certain specific embodiments, the invention provides genetically modified or recombinant *Monascus* strains that are capable of producing increased levels of lactic acid, more particularly L-lactic acid at low pH. More particularly, L-lactic acid is produced at a high yield from hexose and/or pentose sugars.

In particular embodiments, the micro-organism according to the invention comprise a heterologous or exogenous LDH gene. Accordingly, in particular embodiments, the invention provides genetically modified or recombinant *Monascus* strains comprising a heterologous or exogenous LDH gene. In further specific embodiments, the genetically modified or recombinant *Monascus* strains according to the present invention comprise a heterologous or exogenous LDH gene that encodes a functional protein that is at least 80% identical to a protein encoded by SEQ ID NO:1.

The invention further envisages that the yield of organic acids, such as lactic acid, can be further enhanced by inactivating endogenous *Monascus* genes encoding proteins involved in an endogenous metabolic pathway which produces a metabolite other than the organic acid of interest and/or wherein the endogenous metabolic pathway consumes the organic acid. In particular embodiments, the production of the metabolite other than the organic acid of interest is reduced. According to further particular embodiments, the microorganisms according to the invention comprise at least one engineered gene deletion and/or inactivation of an endogenous pathway in which the organic acid is consumed or a gene encoding a product involved in an endogenous pathway which produces a metabolite other than the organic acid of interest.

In more particular embodiments the micro-organisms of the strain *Monascus* according to the invention, are recombinant micro-organisms which comprise one or more of the following: a recombinant gene encoding a foreign gene involved in organic acid production and/or at least one engineered gene deletion and/or inactivation of an endogenous pathway in which the organic acid is consumed and/or a gene encoding an enzyme involved in an endogenous pathway which produces a metabolite other than the organic acid of interest.

In particular embodiments, the micro-organisms of the strain *Monascus* according to the invention are recombinant micro-organisms which comprise a recombinant gene encoding Lactic acid dehydrogenase (LDH) and/or at least one engineered gene deletion and/or inactivation of an endogenous lactic acid consumption pathway or a gene encoding an enzyme involved in an endogenous pathway which produces a metabolite other than lactic acid.

In particular embodiments of the invention provide genetically modified or recombinant *Monascus* strains according to the present invention further contain at least one engineered gene or inactivation.

In more particular embodiments, the at least one engineered gene deletion or inactivation is in a gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), 0-lactate dehydrogenase (d-ldh), L-lactate dehydrogenase (l-ldh), lactate 2-monooxygenase and any combination of said genes.

In further embodiments the at least one engineered gene deletion and/or inactivation is in an endogenous gene encoding pyruvate decarboxylase (pdc). More particularly, the gene is an endogenous PDC1, PDC2 and/or PDC4 gene as described herein. In further particular embodiments, the one or more endogenous decarboxylase coding sequences that are inactivated and/or deleted are sequences corresponding to one or more of SEQ ID NO: 3, SEQ ID NO: 4 and/or SEQ NO: 5.

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase. More particularly, the engineered gene deletion or inactivation is an inactivation of the gene comprising the coding sequence SEQ ID NO:2 and/or SEQ ID NO: 6.

In particular embodiments, the micro-organisms according to the invention are capable of producing the organic acid at a yield of at least 0.5 g/L from hexose or pentose sugars or combinations of hexose and pentose sugars. More particularly, the yield is at least 2 g/L, most particularly at least 5 g/L. In particular embodiments the conversion yield of consumed sugar to organic acid is at least 50%.

Particular embodiments of the invention provide genetically modified or recombinant *Monascus* strains according to the present invention, which are capable of producing lactic acid, such as L-lactic acid, from hexose and/or pentose sugars at a yield of at least 2 g/L. In particular embodiments, ethanol is formed as a by-product.

In a further aspect, the present invention relates to the use of the micro-organisms provided herein in the industrial production of organic acids and/or products derived therefrom, more particularly for the industrial production of an organic acid at a pH which is less than 1.5 units above the pKa value of the organic acid. Typically this implies production of an organic acid at a pH which is less than 5, more particularly at a pH which is about 4 or less. Indeed, as a result of their tolerance to organic acids at low pH the microorganisms described herein are particularly suitable for the high yield production of organic acids without conversion into the ion salt. In this context, genetically modified strains capable of producing organic acids with increased yield at low pH are of particular interest. Indeed, the micro-organisms of the present invention are capable of ensuring a high yield at limited production costs. Accordingly, in particular embodiments the invention provides high yield methods of producing a composition comprising an organic acid comprising the steps of (i) providing a genetically modified or recombinant micro-organism according to the invention, and (ii) culturing said micro-organism at a pH of 2.8 in the presence of a hexose or pentose sugars or combinations thereof as the sole carbon source. The compositions obtained by the methods of the present invention contain high levels of lactic acid at low pH without contaminating organic nutrients typically required for the cultivation of some micro-organisms.

In particular embodiments, methods for producing an organic acid at high yield are provided which comprise the steps of (i) providing a genetically modified or recombinant strain of a species within the *Monascus* genus that is tolerant to high organic acid concentration at low pH and which has been modified to produce an organic acid at high yield from hexose or pentose sugars or combinations of hexose and pentose sugars and (ii) culturing said strain in the presence of hexose or pentose sugars or combinations of hexose and pentose sugars. In particular embodiments, the methods according to the present invention further comprise the step of recovering the organic acid.

In particular embodiments of the methods of the present invention, the produced organic acid is lactic acid. In more particular embodiments, the lactic acid is L-lactic acid.

In certain embodiments, the methods of producing (compositions comprising) organic acid of the present invention result in a yield of organic acid that is at least 2 g/L. In further particular embodiments, the titer of organic acid is between 50-100 g/L and the productivity is at least 1 g/L/hr, more particularly between 2-3 g/L/hr.

BRIEF DESCRIPTION OF THE FIGURES

The present invention is illustrated by the following Figures which are to be considered as illustrative only and do not in any way limit the scope of the invention.

FIG. 4 illustrates the sequence of the codon optimized Bt-L-LDH gene.

FIG. 14A illustrates the sugar (glucose or xylose) consumption and product (ethanol and lactic acid) formation by wild type LF5 under severely aerobic conditions.

FIG. 14B illustrates the sugar (glucose or xylose) consumption and product (ethanol and lactic acid) formation by wild type LF5 under severely anaerobic conditions.

FIG. 14C illustrates the sugar (glucose or xylose) consumption and product (ethanol and lactic acid) formation by transformant 5t2 under severely aerobic conditions.

FIG. 14D illustrates the sugar (glucose or xylose) consumption and product (ethanol and lactic acid) formation by transformant 5t2 under severely anaerobic conditions.

FIG. 14E illustrates the sugar (glucose or xylose) consumption and product (ethanol and lactic acid) formation by transformant 5t21 under severely aerobic conditions.

FIG. 14F illustrates the sugar (glucose or xylose) consumption and product (ethanol and lactic acid) formation by transformant 5t21 under severely anaerobic conditions.

FIG. 15A illustrates the sugar (glucose or xylose) consumption and product (ethanol and lactic acid) formation by wild type LF6 under severely aerobic conditions.

FIG. 15B illustrates the sugar (glucose or xylose) consumption and product (ethanol and lactic acid) formation by wild type LF6 under severely anaerobic conditions.

FIG. 15C illustrates the sugar (glucose or xylose) consumption and product (ethanol and lactic acid) formation by transformant 6t4 under severely aerobic conditions.

FIG. 15D illustrates the sugar (glucose or xylose) consumption and product (ethanol and lactic acid) formation by transformant 6t4 under severely anaerobic conditions.

FIG. 15E illustrates the sugar (glucose or xylose) consumption and product (ethanol and lactic acid) formation by transformant 6t5 under severely aerobic conditions.

FIG. 15F illustrates the sugar (glucose or xylose) consumption and product (ethanol and lactic acid) formation by transformant 6t5 under severely anaerobic conditions.

FIG. 16 illustrates the sequence of the *Monascus ruber* PDC1 open reading frame.

FIG. 17 illustrates the sequence of the *Monascus ruber* PDC2 open reading frame.

FIG. 24 illustrates the sequence of the *Monascus ruber* PDC4 open reading frame (SEQ ID No: 5).

FIG. 26 illustrates the sequence of the *Monascus ruber* CYB2 open reading frame. (SEQ ID NO:2); a putative intron in the genomic sequence is indicated by small letters.

FIG. 27A illustrates the first 920 nucleotides of the sequence of the *Monascus ruber* Mona00569 gene encoding cytochrome dependent L-LDH (SEQ ID No: 6).

FIG. 27B illustrates the remaining 735 nucleotides of the sequence of the *Monascus ruber* Mona00569 gene encoding cytochrome dependent L-LDH (SEQ ID No: 6).

DETAILED DESCRIPTION OF THE INVENTION

Figure 1:
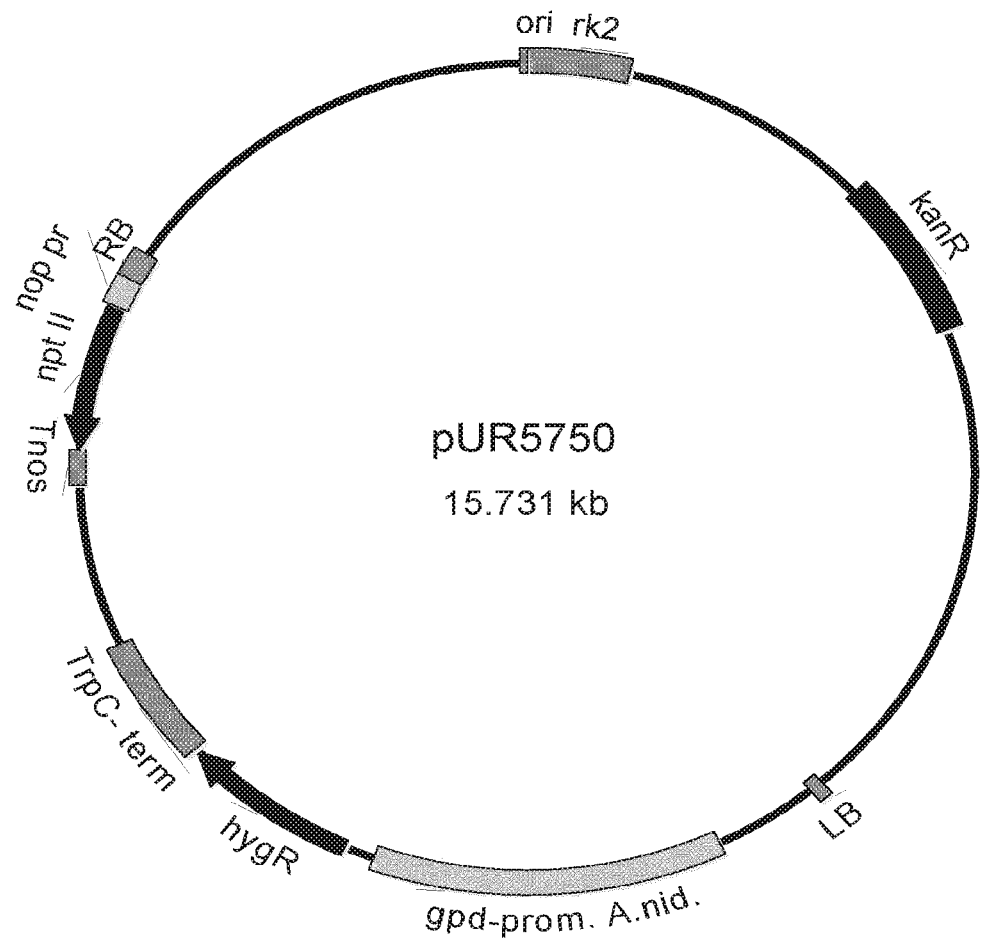
FIG. 1 illustrates an example of a transformation vector which can be used for the transformation of *Monascus* strains according to particular embodiments of the invention.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this implies that embodiments are also envisaged which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +1-0.1% or less of and from the specified value, insofar such variations are appropriate to perform in the disclosed invention. It is to be understood that the value to which the modifier "about" refers is itself also specifically, and preferably, disclosed.

As used herein, the term "homology" denotes structural similarity between two macromolecules, particularly between two polypeptides or polynucleotides, from same or different taxons, wherein said similarity is due to shared ancestry. Hence, the term "homologues" denotes so-related macromolecules having said structural similarity.

All documents cited in the present specification are hereby incorporated by reference in their entirety.

As used herein, sequence identity between two polypeptides can be determined by optimally aligning (optimal alignment of two protein sequences is the alignment that maximises the sum of pair-scores less any penalty for introduced gaps; and may be preferably conducted by computerised implementations of algorithms, such as "Clustal W using the alignment method of Wilbur and Lipman, 1983 (Proc. Natl. Acad. Sci. USA, 80: 726-730). Alternative methods include "Gap" using the algorithm of Needleman and Wunsch 1970 (J Mol Biol 48: 443-453), or "Bestfit", using the algorithm of Smith and Waterman 1981 (J Mol Biol 147: 195-197), as available in, e.g., the GCG™ v. 11.1.2 package from Accelrys) the amino acid sequences of the polypeptides and scoring, on one hand, the number of positions in the alignment at which the polypeptides contain the same amino acid residue and, on the other hand, the number of positions in the alignment at which the two polypeptides differ in their sequence. The two polypeptides differ in their sequence at a given position in the alignment when the polypeptides contain different amino acid residues at that position (amino acid substitution), or when one of the polypeptides contains an amino acid residue at that position while the other one does not or vice versa (amino acid insertion or deletion). Sequence identity is calculated as the proportion (percentage) of positions in the alignment at which the polypeptides contain the same amino acid residue versus the total number of positions in the alignment. In particular embodiment the algorithm for performing sequence alignments and determination of sequence identity is one based on the Basic Local Alignment Search Tool (BLAST) originally described by Altschul et al. 1990 (J Mol Biol 215: 403-10), more particularly the "Blast 2 sequences" algorithm described by Tatusova and Madden 1999 (FEMS Microbiol Lett 174: 247-250), such as using defaults settings thereof.

As used herein, "sequence similarity" between two polypeptides can be determined by optimally aligning (see above) the amino acid sequences of the polypeptides and scoring, on one hand, the number of positions in the alignment at which the polypeptides contain the same or similar (i.e., conservatively substituted) amino acid residue and, on the other hand, the number of positions in the alignment at which the two polypeptides otherwise differ in their sequence. The two polypeptides otherwise differ in their sequence at a given position in the alignment when the polypeptides contain non-conservative amino acid residues at that position, or when one of the polypeptides contains an amino acid residue at that position while the other one does not or vice versa (amino acid insertion or deletion). Sequence similarity is calculated as the proportion (percentage) of positions in the alignment at which the polypeptides contain the same or similar amino acid residue versus the total number of positions in the alignment.

The term "organic acid" as used herein refers to an organic compound with acidic properties. More particularly in the context of the present invention organic acid compounds are selected from the group consisting of lactic acid (2-hydroxypropionic acid), succinic acid, furandicarboxylic acid, fumaric acid, maleic acid, citric acid, glutamic acid, aspartic acid, acrylic acid, oxalic acid, and glucanic acid.

The term "carboxylic acid" refers to an organic acids characterized by the presence of at least one carboxyl group. Acids with two or more carboxyl groups are also referred to as dicarboxylic, tricarboxylic, etc. Examples of carboxylic acids include but are not limited to oxalic acid and mal(e)ic acid, and succinic acid. The term "lactic acid" in this application refers to 2-hydroxypropionic acid in either the free acid or salt form. The salt form of lactic acid is referred to as "lactate" regardless of the neutralizing agent, i.e. calcium carbonate or ammonium hydroxide. As referred to herein, lactic acid can refer to either stereoisomeric form of lactic acid (L-lactic acid or D-lactic acid). The term lactate can refer to either stereoisomeric form of lactate (L-lactate or D-lactate). When referring to lactic acid production this includes the production of either a single stereoisomer of lactic acid or lactate or a mixture of both stereoisomers of lactic acid or lactate. In the particular embodiments where the recombinant fungi of the present invention exclusively produce a single stereoisomer of lactic acid or lactate, the lactic acid or lactate stereoisomer that is produced is said to be "chirally pure". The phrase "chirally pure" indicates that there is no detectable contamination of one stereoisomeric form of lactic acid or lactate with the other stereoisomeric form (the chiral purity of the specified stereoisomer is at least, greater than (or greater than or equal to) 99.9%). The organism according to the present invention have been found to be highly tolerant to organic acids at low pH.

As used herein the terms "tolerance to high organic acid concentration" and more particularly "tolerance to high lactic acid concentration" refers to the ability of the micro organisms to grow in a medium comprising at least 50 g/L organic acid, or at least 75 g/L but potentially up to more than 100 g/L, or even more than 150 g/L, such as 175 g/L or 200 g/L. In particular embodiments, the term "high organic acid concentration", may refer to a saturated solution of the organic acid.

As used herein the term "low pH", refers to a pH of between 2.0 and 5.0, such as less than 4.0, more particularly less than 3.0, more particularly a pH of 2.8 or less.

It will be understood to the skilled person that when referring to a tolerance to an organic acid at a low pH, of particular relevance is the ability to tolerate an organic acid at a pH which corresponds to or is lower than the pKa value of the organic acid, more particularly at a pH which is between 1.5 unit higher and 1.5 unit lower than the pKa value of the organic acid. Where the organic acid has two pKa values (due to the presence of two acid groups), the relevant pKa is the lowest pKa value.

"Lactate dehydrogenase activity" as used herein refers to the ability of the protein to catalyze the reaction of pyruvate to lactate. Lactate dehydrogenase enzymes include (but are not limited to) the enzymes categorized by the Enzyme Commission numbers EC1.1.1.27 and EC1.1.1.28.

The terms "recombinant" or "genetically modified" as used herein with reference to host organisms, microorganisms or cells, encompass such host organisms, microorganisms or cells into which a nucleic acid molecule has been introduced or which has been in another way genetically modified, as well as the recombinant progeny of such host organisms, microorganism or cells. This includes both organisms in which endogenous gene sequences are introduced at a position other than their natural position in the genome and organisms in which endogenous gene sequences have been modified or deleted.

The term "recombinant" as used herein with reference to a nucleotide sequence present in a host organisms, microorganism or cell refers to a nucleotide sequence which is not naturally present in said organisms, microorganism or cell. This includes nucleotide sequences which are foreign to said organisms, microorganism or cell and nucleotide sequences which are introduced at a position other than their natural position in the genome and endogenous gene sequences have been modified.

The term "transformation" encompasses the introduction or transfer of a foreign nucleic acid such as a recombinant nucleic acid into a host organism, microorganism or cell. The so-introduced nucleic acid or the resulting deletion of endogenous nucleic acid is preferably maintained throughout the further growth and cell division of said host organism, microorganism or cell. Any conventional gene transfer or genetic modification methods may be used to achieve transformation, such as without limitation electroporation, electropermeation, chemical transformation, lipofection, virus- or bacteriophage-mediated transfection, etc. The term "gene" as generally used herein refers to a sequence which contains a coding sequence a promoter and any other regulatory regions required for expression in a host cell.

As used herein, the term "promoter" refers to an untranslated sequence located within 50 bp upstream the transcription start site and which controls the start of transcription of the structural gene. Generally it is located within about 1 to 1000 bp, preferably 1-500 bp, especially 1-100 bp upstream (i.e., 5') to the translation start codon of a structural gene. Similarly, the term "terminator' refers to an untranslated sequence located downstream (i.e., 3') to the translation stop codon of a structural gene (generally within about 1 to 1000 bp, more typically 1-500 base pairs and especially 1-100 base pairs) and which controls the end of transcription of the structural gene. A promoter or terminator is "operatively linked" to a structural gene if its position in the genome relative to that of the structural gene is such that the promoter or terminator, as the case may be, performs its transcriptional control function.

As used herein, the term "heterologous" or "exogenous" refers to the fact that the gene or coding sequence under consideration is not native or endogenous to the host.

The term "native" or "endogenous" is used herein with respect to genetic materials (e.g., a gene, promoter or terminator) that are found (apart from individual-to-individual mutations which do not affect function) within the genome of wild-type cells of the host strain.

By "encoding" is meant that a nucleic acid sequence or part(s) thereof corresponds, by virtue of the genetic code of an organism in question, to a particular amino acid sequence, e.g., the amino acid sequence of a desired polypeptide or protein. By means of example, nucleic acids "encoding" a particular polypeptide or protein may encompass genomic, hnRNA, pre-mRNA, mRNA, cDNA, recombinant or synthetic nucleic acids.

Preferably, a nucleic acid encoding a particular polypeptide or protein may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide. Hence, the term may be synonymous with "coding sequence" as used in the art.

The micro-organisms of the order of *Monascus* according to the present invention, have an excellent tolerance to high organic acid concentrations at low pH. More particularly, they are tolerant to organic acids at a pH which is less than 1.5 units higher than the (lowest) pKa value of the organic acid. In particular embodiments, the micro-organisms are tolerant to all organic acids. Most particularly they are tolerant to high concentrations of carboxylic organic acids at low pH.

The tolerance to organic acids of the micro-organisms according to the present invention makes them particularly suitable for use in the industrial production of organic acids such as, but not limited to lactic acid. While in practice in an industrial setting the organic acid of interest may be extracted during production such that extremely high concentrations are not maintained, the tolerance of the strain to the organic acid will nevertheless be advantageous. More particularly, it is of interest to be able to maintain the strain at a pH value which is less than 1.5 above the (lowest) pKa value of the organic acid of interest, most particularly, where the micro-organism is tolerant to the organic acid at a pH which is less than the (lowest) pKa value of the organic acid of interest. The pKa values of organic acids vary between about 3.5 and 6. A non-limiting list of exemplary organic acids, their pKa values and the corresponding pH range at which the organisms are preferably grown for industrial production of the organic acid is provided in Table 1.

TABLE 1 exemplary organic acids

| Organic acid | pKa | pH range |
|---|---|---|
| Lactic acid | 3.85 | 2.5-5 |
| Malic acid | 3.4-5.11 | 2.0-4.5 |
| Succinic acid | 4.16-5.66 | 3.0-5.5 |
| Acrylic acid | 4.25 | 3-5.5 |
| Citric acid | 3.13-4.76, 6.4 | 2.0-4.5 |

The organisms according to the present invention have been found to be tolerant to a range of organic acids, at low pH. In particular embodiments, they are tolerant to carboxylic acids, at a pH which is lower than 1.5 units above the (lowest) pKa value of the organic acid. In particular embodiments, the tolerance to organic acids which do not contain a double bonded $CH_2$ group is increased. In further particular embodiments, the micro-organisms are tolerant to organic acids at a pH which is lower than the pKa value of the relevant organic acid. More particularly, the micro-organisms of the present invention have an exceptional tolerance to lactic acid at a pH of less than 3.

It has moreover been found that the organisms according to the present invention can be engineered to ensure production of an organic acid. More particularly they can be engineered to ferment simple sugars to an organic acid at high yield. The fact that in particular embodiments these organisms can be cultivated under anaerobic or quasi-anaerobic conditions, provides an additional advantage in the context of industrial production methods.

The micro-organisms according to the invention are of a species within the *Monascus* genus. It has surprisingly been found that *Monascus* strains can be identified which are tolerant to high organic acid concentrations at low pH. Typically the micro-organisms represent a strain of a species that is chosen from the group comprising *Monascus albidulus, Monascus argentinensis, Monascus aurantiacus, Monascus barkeri, Monascus bisporus, Monascus eremophilus, Monascus floridanus, Monascus fuliginosus, Monascus fumeus, Monascus kaoliang, Monascus lunisporas, Monascus mucoroides, Monascus olei, Monascus pallens, Monascus paxii, Monascus pilosus, Monascus pubigerus, Monascus purpureus, Monascus ruber, Monascus rubropunctatus, Monascus rutilus, Monascus sanguineus, Monascus serorubescens* and *Monascus vitreus*. In particular embodiments of the present invention, the micro-organisms of the present invention are strains of the species *Monascus ruber*.

Exemplary strains according to the present invention, referred to herein also as LF4, LF5 and LF6, have been deposited at the Centraalbureau voor Schimmelcultures (CBS) in Utrecht, The Netherlands and have been attributed the accession numbers CBS 127564, CBS 127565 and CBS 127566, respectively.

In particular embodiments, the invention relates to micro-organisms of the order of *Monascus* as described above, which have been genetically engineered to improve organic acid yield, more particularly the production of an organic acid, such as lactic acid from simple sugars such as hexose or pentose sugars or combinations of hexose and pentose sugars. This can be achieved in different ways, which are not mutually exclusive.

In particular embodiments, the genetic engineering techniques envisaged in the context of the present invention aim at the increase organic acid production by expression of an (exogenous) gene encoding an enzyme involved in the production of the organic acid of interest.

In particular embodiments, the organic acid of interest is lactic acid. More particularly, overexpression of an (exogenous) lactate dehydrogenase gene is envisaged. Lactate dehydrogenase catalyzes the last step in the conversion of sugars to lactic acid, whereby pyruvate is converted to lactate. Increased expression and/or activity of LDH genes thus ensures an increase in lactic acid yield. Accordingly, in particular embodiments, the invention provides genetically modified or recombinant *Monascus* strains comprising at least one functional lactate dehydrogenase (LDH) gene integrated into its genome. In particular embodiments, the LDH gene comprises a heterologous or exogenous LDH coding sequence.

The introduction of an exogenous LDH gene enables the modified *Monascus* strain to produce increased quantities of the L- and/or D-lactic acid stereoisomer. According to certain particular embodiments of the present invention, the genetically modified or recombinant micro-organisms of the order of *Monascus* comprise (or exclusively contain) one or more exogenous L-LDH genes (and not an exogenous D-LDH gene), so that the organisms produces an optically or chirally pure L-lactic acid. Alternatively, production of chirally pure D-lactic acid can be envisaged by introduction of an exogenous D-LDH gene. In specific embodiments of the present invention the genetically modified or recombinant organisms of the present invention of the order of *Monascus* contain one or more exogenous L-LDH coding sequence and one or more exogenous D-LDH coding sequences, so that the recombinant strain produces a racemic mixture of L and 0-lactic acid.

The exogenous LDH gene used in the context of the present invention, is a gene that encodes for a lactate dehydrogenase enzyme or an active fragment thereof, i.e. a protein having lactate dehydrogenase activity.

In particular embodiments, the exogenous LDH gene or coding sequence is a gene or coding sequence derived from another organism that has been genetically modified (e.g. codons altered) for improved expression in *Monascus*.

In the context of the present invention, suitable LDH genes include those obtained from bacterial, fungal, yeast or mammalian sources. Examples of specific L-LDH genes are those obtained from *Lactobacillus helveticus, L. casei, Bacillus megaterium, Pediococcus acidilactici, Rhizopus oryzae* and mammal sources such as bovine or swine. In particular *Bos taurus*. Examples of specific D-LDH genes are those obtained from *L. helveticus, L. johnsonii, L. bulgaricus, L. delbrueckii, L. plantarum, L. pentosus* and *P. acidilactici*. Functional coding sequences that have an identity score of at least 70% relative to the coding sequences in these genes at the amino acid level and encode functional proteins are suitable. The native genes obtained from any of these sources may be subjected to mutagenesis if necessary to provide a coding sequence starting with the usual eukaryotic starting codon (ATG), or for other purposes. In particular embodiments, the L-LDH gene is that obtained from *L. helveticus* or one that has a sequence identity therewith of at least 80%, 85%, 90% or 95%. According to other specific embodiments, the L-LDH gene that is obtained from *B. megaterium* or one at least 80%, 85%, 90% or 95% compared with such gene. According to further certain particular embodiments, the L-LDH gene is that obtained from *Bos taurus* or one that has an identities score of at least 80%, 85%, 90% or 95% compared with such gene. In particular embodiments, the D-LDH gene is that obtained from *L. helveticus* or one that has an identity score of at least 80%, 85%, 90% more particularly at least 95% compared with such gene.

Particularly suitable LDH coding sequences include those that encode for an enzyme with an amino acid sequence that has an identity score of at least 80%, 85% or 95%, compared with the sequence identified as SEQ. ID. NO. 1. Particularly suitable LDH genes also include those that encode a functional enzyme having a protein sequence that has an identities score of at least, 80%, 85% or 95% compared to the protein sequence encoded by SEQ ID NO:1; in particular embodiments suitable LDH genes include those that encode a functional enzyme and having a sequence that with an identities score of at least, 80%, 85% or 95% compared to the sequence of SEQ ID NO:1 or identical to SEQ ID NO:1. The genetically modified or recombinant *Monascus* strains of the present invention may contain a single exogenous gene encoding an enzyme involved in the production of the organic acid of interest or multiple exogenous genes. Thus, for instance, the recombinant strain may comprise a single exogenous LDH gene or multiple exogenous LDH genes, such as from 1 to 10 exogenous LDH genes, especially from 1 to 5 exogenous LDH genes. When the transformed strain contains multiple exogenous LDH genes, the individual genes may be copies of the same gene, or include copies of two or more different LDH genes. Multiple copies of the exogenous LDH gene may be integrated at a single locus (so they are adjacent to each other), or at several loci within the genome of the host strain.

In further particular embodiments, the organic acid of interest is succinic acid. More particularly, overexpression of an (exogenous) phosphoenolpyruvate (PEP) carboxylase gene (ppc) and/or overexpression of (exogenous) fumarate reductase (frdABCD) and/or overexpression of pyruvate carboxylase and/or overexpression of malic enzyme is envisaged activity.

Malic enzyme catalyzes the conversion of pyruvate to succinic acid via Malic acid, while fumarate reductase converts fumaric acid to succinic acid. Increased expression and/or activity of these genes thus ensures an increase in succinic acid yield.

Further examples of recombinant enzymes which can be used to increase the production of an organic acid of interest are known to the skilled person The recombinant coding sequence encoding the enzyme of interest is placed under the transcriptional control of one or more promoters and one or more terminators, both of which are functional in the modified fungal cell.

Promoters and terminator sequences may be native to the *Monascus* host strain or exogenous to the cell. Useful promoter and terminator sequences include those that are highly identical (i.e. have an identities score of 90% or more, especially 95% or more, most preferably 99% or more) in their functional portions compared to the functional portions of promoter and terminator sequences, respectively, that are native to the host strain, particularly when the insertion of the exogenous gene is targeted at a specific site in the strain's genome.

In particular embodiments the promoter has an identity score at least 90%, 95% or 99% relative to a promoter that is native to a fungal gene. More particularly the promoter has an identity score of at least 90%, 95% or 99% compared to a promoter for a gene that is native to the *Monascus* host strain. In particular embodiments, the terminator has an identity score of at least 90%, 95% or 99% compared to a terminator for a gene that is native to a fungus. The terminator may have an identity score of at least 90%, 95% or 99% with a terminator for a gene that is native to the *Monascus* host strain. The use of native (to the host strain) promoters and terminators, together with their respective upstream and downstream flanking regions, can permit the targeted integration of the recombinant gene into specific loci of the host strain's genome, and for simultaneous integration the recombinant gene and deletion of another native gene. It is possible for the different exogenous coding sequences such as the LDH coding sequences to be placed under the control of different types of promoters and/or terminators.

The recombinant gene may be integrated randomly into the host strain's genome or inserted at one or more targeted locations. Examples of targeted locations include the loci of a gene that is desirably deleted or disrupted.

The present inventors further envisage increasing organic acid production in the micro-organisms of the order of *Monascus* according to the invention, by limiting the production of metabolites endogenous to the host and/or reducing endogenous consumption of the organic acid of interest. Indeed, this not only prevents the waste of material and energy by the host, but pushes the host to fully rely on the production pathway of the enzyme of interest created by introduction of the recombinant gene.

In fungi such as *Monascus*, lactic acid is consumed in the presence of oxygen. This is ensured by the cytochrome dependent lactate dehydrogenase. Accordingly, additionally or alternatively, according to particular embodiments of the present invention, the micro-organisms are modified to reduce endogenous consumption of lactic acid. More particularly, this is ensured by reducing expression of the endogenous LDH gene. This increases lactic acid yield under aerobic conditions.

Thus, according to a particular embodiment, the micro-organisms of the present invention have one or more inactivated endogenous cytochrome-dependent LDH gene. The present inventors have identified and characterized endogenous LDH genes from *Monascus ruber*. In particular embodiments, the endogenous LDH comprises the coding sequence of SEQ ID NO: 2 or SEQ ID NO: 6. As detailed herein below nucleotide sequences derived from the coding, non-coding, and/or regulatory sequences of the endogenous LDH gene of *Monascus ruber* can be used to prevent or reduce expression of LDH in *Monascus*.

In further particular embodiments, the genetic engineering techniques used in the context of the present invention are aimed at reducing the endogenous production of metabolites other than the organic acid of interest. More particularly, recombinant micro-organisms are provided which are characterized in that enzymatic activities involved in the production of metabolites other than lactic acid such as ethanol have been inactivated or suppressed.

In this context it is meant by "inactivate" that all or part of the coding region of the gene is eliminated (deletion), or the gene or its promoter and/or terminator region is modified (such as by deletion, insertion, or mutation) so that the gene no longer produces an active enzyme, or produces an enzyme with severely reduced activity. Inactivation further includes silencing such as by antisense, triple helix, and ribozyme approaches, all known to the skilled person.

According to particular embodiments, the genetically modified or recombinant *Monascus* strains according to the present invention comprise at least one engineered gene deletion and/or inactivation, more particularly in an endogenous gene encoding an enzyme involved in the ethanol production pathway. In these embodiments, the at least one engineered gene deletion or inactivation can for example be in an endogenous gene encoding an enzyme that is involved in ethanol production pathway or in the production of other metabolites than the organic acid of interest in the host strain, such as a gene encoding an enzyme selected from the group consisting of pyruvate decarboxylase (pdc), fumarate reductase, alcohol dehydrogenase (adh), acetylaldehyde dehydrogenase, phosphoenolpyruvate carboxylase (ppc), D-lactate dehydrogenase (d-ldh), L-lactate dehydrogenase (l-ldh), lactate 2-monooxygenase and any combination of said genes. In more particular embodiments, the at least one engineered gene deletion and/or inactivation can be in an endogenous gene encoding pyruvate decarboxylase (pdc). Pyruvate decarboxylase catalyses the first step in the alcohol pathway. Accordingly micro-organisms having a substantially reduced pyruvate decarboxylase (PDC) activity are particularly envisaged. The term "reduced pyruvate decarboxylase activity" means either a decreased concentration of enzyme in the cell (as a result of at least one genetic modification affecting expression) and/or reduced or no specific catalytic activity of the enzyme (as a result of at least one genetic modification affecting activity).

In particular embodiments, the invention provides microorganisms of the order of *Monascus* wherein the pyruvate decarboxylase activities approach zero or are reduced compared to the normal pyruvate decarboxylase activities in wild type strains. Accordingly, in particular embodiments the pyruvate decarboxylase activities in the strains of the present invention are for instance at least 60% lower, preferably at least 80% lower and even more preferably at least 90% lower than the pyruvate decarboxylase activity detectable in of wild type strains.

In particular embodiments, the invention provides microorganisms comprising one or more inactivated endogenous pyruvate decarboxylase genes. The present inventors have identified and characterized endogenous pyruvate decarboxylase genes from *Monascus ruber*. In particular embodiments, the endogenous pdc gene comprises the coding sequence of SEQ ID NO: 3 or SEQ ID NO: 4 or SEQ ID NO:5. In particular embodiments, the invention provides *Monascus ruber* strains in which all three pdc genes are inactivated or deleted. As detailed herein below nucleotide sequences derived from the coding, non-coding, and/or regulatory sequences of one or more of the endogenous pdc genes of *Monascus ruber* can be used to prevent or reduce expression of pdc in *Monascus*.

According to particular embodiments of the present invention, strains are provided, which are characterized by the feature that the ethanol production by said strain approaches zero or is at least reduced compared to the background ethanol production in the wild-type strain. Accordingly, in particular embodiments, the ethanol production in the strains of the present invention is for instance at least 60% lower, preferably at least 80% lower and even more preferably at least 90% lower than the ethanol production in the corresponding wild-type strain.

According to particular embodiments, the genetically modified or recombinant *Monascus* strains according to the present invention are further modified to improve consumption of pentose sugars, more particularly xylose consumption. This can be achieved in different ways. In particular embodiments this is achieved by introduction into the organism, a nucleic acid sequence encoding xylose isomerase. Such a nucleic acid can be from different origins, more particularly from a eukaryote, most particularly from a an anaerobic fungus. In a particular embodiment the xylose isomerase originates from *Pyromyces* sp., from a *Clostridium* or a *Fusobacterium* or from *Bacteroides thetaiotaomicron* or *Cyllamyces*. Examples of suitable xylose isomerase genes are known in the art and include but are not limited to xylose isomerase from *Piromyces* sp. When expressed, the sequence encoding the xylose isomerase confers to *Monascus* the ability to convert xylose to xylulose which may be further metabolised by *Monascus* in the production of the organic acid of interest. Thus, *Monascus* is capable of growth on xylose as carbon source, more particularly is capable of producing the organic acid of interest with xylose as a carbon source, or in particular embodiments, with xylose as the only carbon source.

In further particular embodiments, the recombinant *Monascus* strain is modified by introduction into the organism, a nucleic acid sequence encoding xylose reductase and/or xylitol dehydrogenase. Such a nucleic acid can be from different origins, more particularly from a eukaryote, most particularly from *Pichia stipitis*. When expressed, the sequence encoding the xylose reductase confers to *Monascus* the ability to produce an organic acid from xylulose.

Genetic modification of the host strains is accomplished in one or more steps via the design and construction of appropriate vectors and transformation of the host strain with those vectors. Electroporation and/or chemical (such as calcium chloride- or lithium acetate-based) transformation methods or *Agrobacterium tumefaciens*-mediated transformation methods as known in the art can be used. The vectors can either be cut with particular restriction enzymes or used as circular DNA. The vector used for genetic modification of the host strains may be any vector so long as it can integrate in the genome of the host strain. Vectors of the present invention can be operable as cloning vectors or expression vectors in the selected host strain. Numerous vectors are known to practitioners skilled in the art, and selection of an appropriate vector is a matter of choice. The vectors may, for example, be the pUR5750 transformation vector, the pCGHT3 transformation vector . . . etc.

In general, a vector is prepared that contains the coding sequence of interest and associated promoter and terminator sequences. The vector may contain restriction sites of various types for linearization or fragmentation. Vectors may further contain a backbone portion (such as for propagation in *E. coli*) many of which are conveniently obtained from commercially available yeast or bacterial vectors. The vector preferably contains one or more selection marker gene cassettes. A "selection marker gene" is one that encodes a protein needed for the survival and/or growth of the transformed cell in a selective culture medium. Typical selection marker genes encode proteins that (a) confer resistance to antibiotics or other toxins such as zeocin (sh ble gene from *Streptoalloteichus hindustanus*), genetecin, melibiase (MEL5), hygromycin (aminoglycoside antibiotic resistance gene from *E. coli*), ampicillin, tetracycline, or kanamycin (kanamycin resistance gene of Tn903), (b) complement auxotrophic deficiencies of the cell. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3-) cannot grow on media lacking uracil. Thus a functional UBA3 gene can be used as a marker on a cell having a uracil deficiency, and successful transformants can be selected on a medium lacking uracil. Only cells transformed with the functional URA3 gene are able to synthesize uracil and grow on such medium. If the wild-type strain does not have a uracil deficiency (as is the case with I. orientalis, for example), an auxotrophic mutant having the deficiency must be made in order to use URA3 as a selection marker for the strain. Methods for accomplishing this are well known in the art.

Preferred selection makers include the zeocin resistance gene, G418 resistance gene, hygromycin resistance gene. The selection marker cassette typically further includes a promoter and terminator sequence, operatively linked to the selection marker gene, and which are operable in the host *Monascus* strain.

Successful transformants can be selected for in known manner, by taking advantage of the attributes contributed by the marker gene, or by other characteristics (such as ability to produce lactic acid, inability to produce ethanol, or ability to grow on specific substrates) contributed by the inserted genes. Screening can be performed by PCR or Southern analysis to confirm that the desired insertions and deletions have taken place, to confirm copy number and to identify the point of integration of genes into the host strain's genome. Activity of the enzyme encoded by the inserted gene and/or lack of activity of enzyme encoded by the deleted gene can be confirmed using known assay methods.

The deletions or inactivations envisaged herein can be accomplished by genetic engineering methods, forced evolution or mutagenesis and/or selection or screening. Indeed, the present state of the art provides a wide variety of techniques that can be used for the inactivation, deletion or replacement of genes. Such molecular techniques include but are not limited to:

(i) gene inactivation techniques based on natural gene silencing methods including antisense RNA, ribozymes and triplex DNA formation, (ii) techniques for single gene mutation such as gene inactivation by single crossing over with non-replicative plasm id and gene inactivation with a non replicative plasmid or a linerized DNA fragment capable of double-crossover chromosomal integration (Finchham, 1989, Microbiological Reviews, 53: 148-170; Archer et al., 2006, Basic Biotechnology: 95-126), and (iii) techniques for multiple unmarked mutations in the same strain, such as but not limited to:

(a) deletion and replacement of the target gene by an antibiotic resistance gene by a double crossover integration through homologous recombination of an integrative plasmid, giving segregationally highly stable mutants;

(b) removing of the antibiotic resistance gene with the Flp recombinase system from *Saccharomyces cerevisiae* allowing the repeated use of the method for construction of multiple, unmarked mutations in the same strain and (c) generating a strain deleted for the upp gene, encoding uracil phosphoribosyl transferase, thus allowing the use of 5-fluorouracyl as a counter selectable marker and a positive selection of the double crossover integrants.

In particular embodiments the deletion or disruption of the endogenous gene is performed according to the method described by Oliveira et al (2008) (Appl Microbiol Biotechnol 80, 917-924)

In particular non-limiting embodiments of the present invention, the deletion or disruption of the endogenous gene, may include the introduction of one or more functional structural genes, notably a gene encoding an enzyme involved in the production of the organic acid of interest, such as an LDH gene as described above, inserted between the 5' and 3' flanking portions of one of the endogenous genes of the host strain. The functional gene preferably includes functional promoter and terminator sequences operatively linked to the structural gene. This approach allows for the simultaneous deletion of the endogenous gene and insertion of the functional exogenous or heterologous gene. The vector may include a selection marker gene instead of or in addition to the structural gene. Again, the selection marker gene is positioned on the vector between the 5' and 3' flanking portions of the endogenous gene(s) being targeted, and becomes inserted in the locus of the functional endogenous gene. The use of a selection marker gene has the advantage of introducing a means of selecting for successful transformants. However, it is also possible to select for successful transformants based on the resulting functional characteristics. For instance, depending on the genes deleted and introduced it may be possible to screen on reduced or eliminated ability to grow on specific building blocks, to produce the organic acid of interest at high concentrations or on their reduced ability to produce specific metabolites such as ethanol.

Accordingly, a further aspect of the present invention provides methods of obtaining high yield organic acid producing micro-organisms, which methods comprise
  a) obtaining a micro-organism of the genus of *Monascus* having a high tolerance to the organic acid at low pH;
  b) transforming the micro-organism with one or more recombinant nucleic acid sequences which ensure an increased production of the organic acid and/or a reduction of endogenous production of metabolites; and
  c) Selecting a micro-organism capable of high yield organic acid production.

The step of identifying a micro-organism having a high tolerance to the organic acid at low pH can be obtained by selecting the micro-organism on a medium containing high concentrations of the organic acid. More particularly selection is performed by selection on a medium containing the organic acid at a pH which is less than 1.5 unit more than the (lowest) pKa value of the relevant organic acid. In particular embodiments the pH is less than one unit more than the relevant pKa value. In further particular embodiments the pH is less than the pKa value.

In particular embodiments, the micro-organisms are selected on a medium containing the organic acid at 50 g/L, most particularly 100 g/L, and in particular embodiments the micro-organism are selected on a medium containing the organic acid of up to 150 to 175 g/L In particular embodiments, the organic acid is lactic acid, and the pH is less than 3.8, more particularly less than 3.

It has surprisingly been found by the present inventors that micro-organisms of the order of *Monascus* can be identified which are tolerant to high organic acid concentrations, such as, but not limited to high lactic acid concentrations, at a low pH, more particularly at a pH which is less than the pKa of the organic acid. More particularly it has been found that micro-organisms of the order of *Monascus* can be identified which are tolerant to increased lactic acid concentrations at a pH of less than 3.0.

The step of transforming the micro-organism is described in detail hereinabove. As detailed above, different genetic modifications are envisaged which increase the yield of organic acid production.

The step of selecting a micro-organism capable of high yield organic acid production is a selection step known to the skilled person and includes but is not limited to measuring the activity of enzymes involved in the production of the organic acid of interest by methods such as those described for LDH in the Examples herein. Additionally or alternatively in the methods according to the invention, the selection step can be based on reduced production of ethanol, reduced organic acid consumption, etc. . . . . .

In a further aspect, the present invention provides methods of producing an organic acid, more particularly at high yield. Indeed, high yield production of organic acids is of interest in view of its numerous industrial applications. The methods of the present invention are of interest for the production for organic acids as food or feed additive as acidulant, flavoring agent, pH buffering agent, or preservative, for use in pharmaceuticals and cosmetics and for the production of detergent and polymers. Lactic acid polymers for instance have properties similar to petroleum-derived plastic but have the advantage of being biodegradable and environmentally friendly.

In particular embodiments, the methods of the present invention comprise the steps of obtaining a microorganism of the order of *Monascus* which is tolerant to high concentrations of organic acid at low pH, genetically modifying it to increase yield of the organic acid and culturing the thus obtained micro-organism in the presence of specific substrates or chemical building blocks at a pH of less than 5, more particularly less than 4, more particularly at a pH which is less than 1.5 units above the pKa of the organic acid.

In particular embodiments, the methods of the present invention comprise the steps of (i) obtaining a strain of the order of *Monascus*, which is tolerant to the organic acid at low pH, more particularly at a pH which is less than 1.5 units above the pKa of the organic acid; (ii) modifying said strain such that it is capable of producing the organic acid of interest at high yield from hexose or pentose sugars or combinations of hexose and pentose sugars; and (ii) culturing said strain in the presence of a suitable substrate, more particularly at a pH which is less than 1.5 units above the pKa of the organic acid, most particularly at a pH of less than 5, most particularly less than 4.

In particular embodiments of the methods of the present invention, the produced organic acid is a carboxylic acid, even more particularly lactic acid. Most particularly, the produced organic acid is L-lactic acid.

Methods for obtaining a micro-organism tolerant to organic acids of the order of *Monascus* and methods of modifying said organism to increase organic acid production yield are described hereinabove and illustrated in the Examples section.

In particular embodiments of the process of the invention, the micro-organism or strain of the order of *Monascus* are cultivated in a medium that includes a sugar that is fermentable by the transformed strain. The sugar may be a hexose sugar such as glucose, glycan or other polymers of glucose, glucose oligomers such as maltose, maltotriose and isomaltotriose, panose, fructose, and fructose oligomers. In particular embodiments, the micro-organism is modified to have the ability to ferment pentose sugars, and the medium includes a pentose sugar such as xylose, xylan or other oligomer of xylose. In particular embodiments, the organisms are cultivated on combinations of hexose and pentose sugars.

The sugars can be hydrolysates of a hemicellulose or cellulose-containing biomass. In particular embodiments, the micro-organism is modified to ensure degradation of the biomass to monomers (e.g. expression of cellulase genes). Accordingly, in particular embodiments, the substrate comprises a sugar oligomer or polymer such as cellulose, hem icellulose or pectin.

Additionally or alternatively, enzymes can be added to the cultivation medium to ensure degradation of the substrate into fermentable monomers.

In particular embodiments of the invention, the medium contains at least (the equivalent of) 5 g/L, at least 10 g/L, at least 20 g/L, at least 30 g/L, more particularly at least 40 g/L, and even more particularly at least 50 g/L glucose. In further particular embodiments, the medium comprises at least 100 g/L, more particularly at least 200 g/L.

The medium may optionally contain further nutrients as required by the particular *Monascus* strain, including inorganic nitrogen sources such as ammonia or ammonium salts, and the like, and minerals and the like. However, in more particular embodiments, the medium is a complete mineral medium comprising a pentose or hexose sugar as the only carbon source. The ability of the strains of the present invention to grow on this simple medium greatly reduces cost of cultivation and simplifies purification of the organic acid produced. Other growth conditions, such as temperature, cell density, and the like are not considered to be critical to the invention and are generally selected to provide an economical process. Temperatures during each of the growth phase and the production phase may range from above the freezing temperature of the medium to about 50° C. A preferred temperature, particularly during the production phase, is from about 30-45° C.

The culturing step of the methods of the invention may be conducted aerobically, microaerobically or anaerobically. Quasi-anaerobic conditions or oxygen limited conditions, in which no oxygen is added during the process but dissolved oxygen is present in the medium at the start of the production process, can also be used.

In particular embodiments, the methods of the present invention comprise cultivation of micro-organisms (strains) of the order of *Monascus* which exhibit the ability to convert sugars to an organic acid under anaerobic or oxygen-limited conditions.

The cultivation step of the methods according to this aspect of the invention can be conducted continuously, batch-wise, or some combination thereof.

The yield of organic acid obtained by the tools and methods according to the present invention will depend on the cultivation conditions used.

In certain embodiments, the methods of producing an organic acid according to the present invention result in a yield of organic acid that is at least 0.5 g/L, particularly at least 2 g/L, more particularly at least 4 g/L, even more particularly at least 50 g/L, and most particularly between 50-100 g/L. In further particular embodiments the production yield of about 2-3 g/L/hour.

In particular embodiments the micro-organisms of the present invention are capable of converting at least 50%, more particularly at least 60%, even more particularly 75%, most particularly at least 95%, and up to 100% of the glucose consumed. In practice, the yield obtained in particular embodiments of the methods of the present invention is at least 0.5 g/g sugar, more particularly at least 0.6 g/g sugar, but may be up to 0.95 g/g sugar.

In further embodiments, the invention provides methods for producing an organic acid which, in addition to the steps detailed above further comprise the step of recovering the organic acid of interest. In particular embodiments, recovery of the organic acid from cultivation medium in the methods of the present invention is greatly simplified in view of the fact that the organisms can be grown on a mineral medium containing only sugars as a carbon source. Suitable purification can be carried out by methods known to the person skilled in the art such as by using extraction, ion exchange resins, electrodialysis, nanofiltration, etc. . . . .

The present invention will now be further illustrated by means of the following non-limiting examples.

EXAMPLES

Example 1: Isolation of Three *Monascus ruber* Strains LF4, LF5 and LF6 as Highly Lactic Acid Tolerant Strains The strains were isolated from soil and corn-and-wheat silage by incubation in medium at low pH, increasing lactic acid concentration and varying concentrations of glucose and xylose concentrations.

One strain (LF4) was isolated by incubation in DSMZ402 medium with 50 g/l glucose, 50 g/l xylose and 100 g/l lactic acid at pH 2.8 at 40 C.

Another strain (LF5), was isolated as described for LF4, but at pH 2.4

A third strain (LF6), was isolated by incubation in DSMZ402 medium with 25 g/l xylose and 150 g/l lactic acid at pH 2.8 and 32 C.

These three strains of the order of *Monascus*, more particularly *Monascus ruber* were found to be able to grow at low pH (2-3) in the presence of high lactic acid concentrations (up to 150 g/L).

Lactic acid tolerant strains LF4, LF5 and LF6 were deposited as deposit under the Budapest Treaty by the Food & Biobased Research department of the Stichting Dienst Landbouwkundig Onderzoek, Bomseweilanden 9, 6708 W G Wageningen, Nederland on Jul. 21, 2010 and were attributed deposit numbers CBS 127564, CBS 127565 and CBS 127566, respectively.

Example 2: Stable Transformation with a Selectable Marker Gene

I. Materials and Methods a) Transformation

Most protocols for genetic modification of *Monascus ruber* involve the transformation of protoplasts using electroporation or by combination of $CaCl_2$ and polyethylene glycol. However these methods often had low transformation efficiency and low mitotic stability. A transformation method using *Agrobacterium tumefaciens*-mediated integration of DNA with high efficiency has been reported in *M. ruber* (Yang 2008).

We have used this *Agrobacterium tumefaciens*-mediated transformation system for our *M. ruber* strains LF4, LF5 and LF6 and two selected CBS strains CBS 135.60 and CBS 503.70.

*Agrobacterium* strains containing the binary vector pUR 5750, described by de Groot et. al, 1998, were obtained from Plant Research International, WUR. These were grown at 30° C. for 48 h in minimal medium supplemented with kanamycin (100 μg). The cells ($OD_{600}$~1.0) were washed with induction medium without Acetosyringone (AS) and grown with and without AS for 6 h at 28° C. AS was used for induction of virulence and T-DNA transfer. Conidiaspores of *Monascus ruber* ($10^7$ spores) were collected from PDA plates after 10 days of culture. When conidia were transformed, an equal volume of conidia was mixed with an equal volume of *A. tumefaciens* and plated out on nylon filters placed on induction medium with and without AS. The plates were incubated at 25° C. for 4 days. The filters were then transferred to YM-medium containing 200 μg cefotaxime to kill the *Agrobacterium* cells and 100 μg hygromycin to select for transformants.

After 10-14 days fast growing fungal colonies were transferred to fresh YM plates+hygromycin and cefotaxime. After 5 days of growth the edge of the colony was transferred again to a fresh YM plates+hygromycin and cefotaxime.

Applying this procedure results in hygromycin resistant transformants for each of the selected *Monascus* strains (see Table 2).

TABLE 2

| Number of transformants per *M. ruber* strain | |
|---|---|
| *M. ruber* strain | No. of transformants |
| LF4 | 14 |
| LF5 | 3 |
| LF6 | 2 |
| CBS 503.70 | 4 | b) Stability of the Transformants

The first property of the transformants we have addressed is the genetic stability. With respect to this, two features of genetically modified strains are important:

(i) the target gene has to be integrated into the genome, and (ii) the gene has to stay in place and active even without the selection pressure of the antibiotic Presence of the vector DNA in the transformants was first shown by means of PCR.

DNA was isolated from 7 transformants (5 LF4 transformants and 2 CBS 503.70 transformants) and from three wild type strains (LF4, CBS 503.70 and CBS 135.60) and subjected to a PCR with DNA primers able to show the hygromycin gene.

The DNA of the transformants clearly yield a PCR fragment of the same size as from the control vector DNA while the wild type strain do not show this PCR fragment. This shows the presence of the hygromycin gene in the transformants.

In order to establish integration of the vector DNA in the genomic DNA from the *M. ruber* transformants a Southern blot analysis was performed. Genomic DNA was blotted before and after digestion with a restriction enzyme. The blot was hybridized with a probe showing the presence of the hygromycin gene.

In the lanes with the genomic DNA the signals on the blot coincide with the position of the genomic DNA meaning integration of the hygromycin gene in the genome. In the lanes with the digested DNA the signals are visible on different positions (=different DNA fragments) meaning random integration of the hygromycin gene.

In conclusion, we have established random genomic integration of the vector DNA in the *M. ruber* strains.

In order to test the stability of the transformants without the selective pressure of the antibiotic the strains were grown on PDA (potato dextrose agar) plates. After growth for approx. 14 days a part of the outer edge of the culture was transferred to a fresh PDA plate again without hygromycin. This process was repeated 3 times. Finally a part of the outer edge of the culture was transferred to a fresh PDA plate with hygromycin to see whether the strain was still able to grow in the presence of this antibiotic.

The number of transformants still able to grow on selective plates after this procedure was scored (Table 3).

TABLE 3

*M. ruber* transformants screened for the stability of the hygromycin resistance.

| M. ruber strain | No. of transformants tested | No. of transformants growing on Hyg. after 3 |
|---|---|---|
| LF4 | 14 | 14 |
| LF5 | 3 | 3 |
| CBS 503.70 | 4 | 4 |

A second approach was to collect spores from the plate after 3 transfers without antibiotic selection and compare the number of colonies appearing after spreading the spores on PDA plates with and without hygromycin (selective plates). The spores were filtered through glass wool to minimize contamination with mycelial fragments. If the hygromycin gene is lost or inactivated the number of colonies on selective plates is reduced.

A test with all strains showed no reduction in the number of colonies on selective and non-selective plates.

In conclusion, there is no evidence for instability or inactivation of the introduced gene in the *M. ruber* transformants.

As a final test the Southern blot experiment described before has been repeated with 27 transgenic strains after the sequential transfer on non-selective plates and subsequently growth in medium without selective pressure.

This Southern blot confirmed the presence of the hygromycin gene in the genome of the *M. ruber* ruber transformants after growth in non selective medium.

c) Construction of Transformation Vectors

In order to be able to perform sequential transformations on *M. ruber* strains for instance to introduce multiple genes and/or to combine introduction of genes with knock out events, we set on to construct transformation vectors with other selectable markers.

The vector that has been used in the transformation described in the previous paragraph is the pUR5750 plasmid. FIG. 1 shows a map of this plasmid ("RB"=right border; "LB"=left border; "Hpt"=hygromycin phosphotransferase gene).

Figure 2:
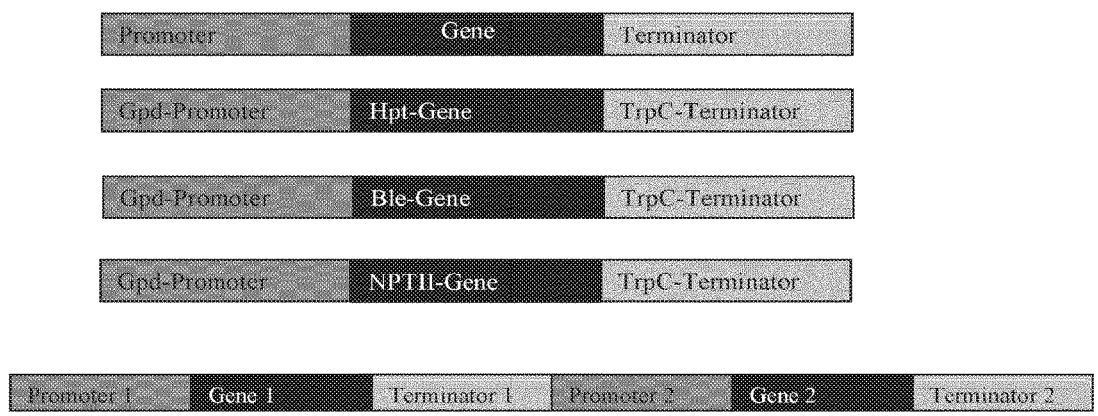
FIG. 2 illustrates an example of a cassette-model for vector construction according to a particular embodiment of the invention.

During transformation the DNA part between the RB (right border) and the LB (left border) is transferred into the fungal genome. On this part the Hpt gene is located. The activity of this gene, under regulation of the gpd-promoter and trpC-terminator, results in hygromycin resistance in transformants. In order to facilitate cloning and exchange of promoters, genes and terminators in this vector we designed a cassette model. As shown in FIG. 2, this cloning strategy enables us to exchange promoters, terminators and genes in the vector but also to combine 2 gene cassettes in a row.

Hpt is the hygromycin phosphotransferase gene giving hygromycin resistance which we already have used. Ble is the bleomycin gene giving phleomycin or zeocin resistance. NptII is the neomycin phosphotransferase gene giving neomycin (G418) resistance.

Since the pUR5750 transformation vector is a large vector, which will become even larger when additional genes are inserted (see FIG. 2), we decided to use also a shorter version of this vector for the transformation of *M. ruber*. In general it is assumed that smaller vectors can be handled more easily during construction and transformation experiments.

Figure 3:
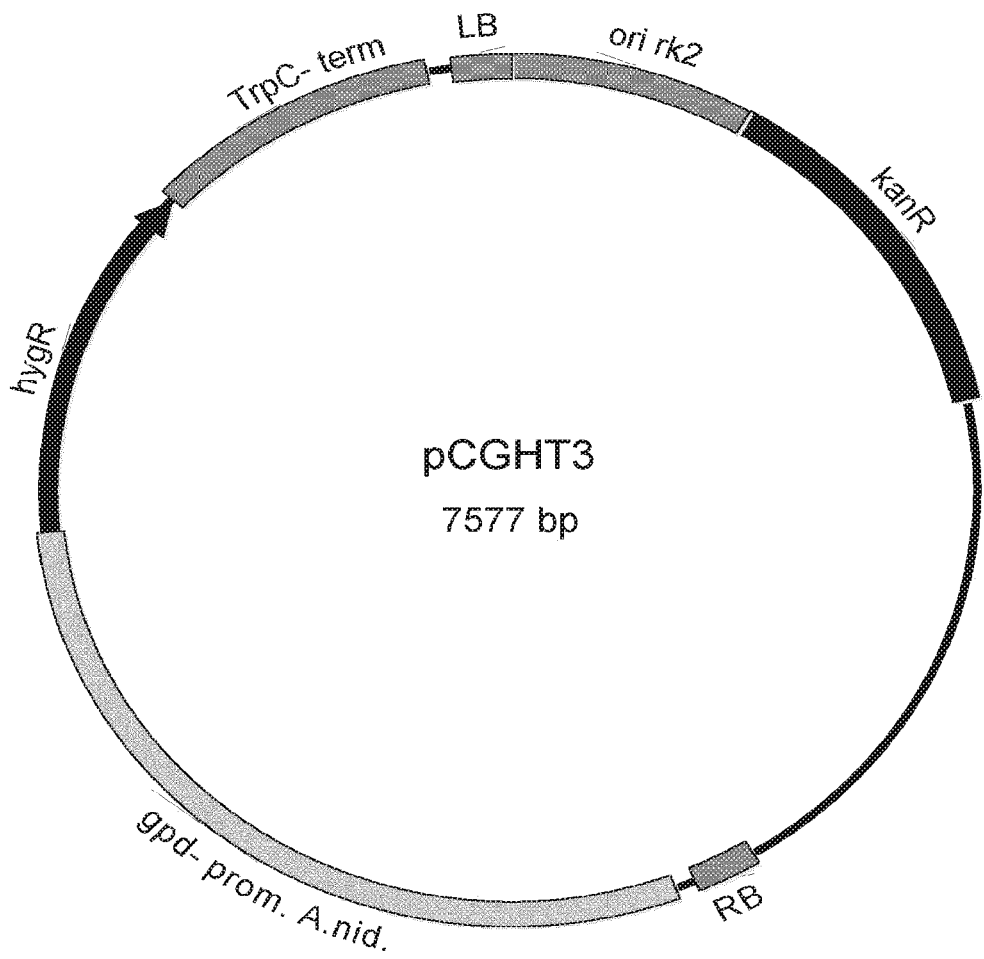
FIG. 3 illustrates the pCGHT3 transformation vector, for use in the transformation of *Monascus* strains according to particular embodiments of the invention.

This smaller vector is a derivative of the pUR5750 and is coded pCB301 (Xiang et al. 1999). Typical DNA elements necessary for plant transformation, the original function of the basic sequence of pUR5750, have been removed from this plasmid leaving a 3574 bp vector. FIG. 3 shows the pCB301 containing the Hpt cassette called pCGHT3 ("RB"=right border; "LB"=left border; "Hpt"=hygromycin phosphotransferase gene). This vector is half the size of the original Hpt vector.

In order to be able to use a selectable marker like the Ble or the NptII gene we first confirmed inability of *Monascus ruber* to grow in media containing concentrations of Zeocin or G418 mostly used in fungal transformation systems. Conidia and spores from *Monascus ruber* strain LF4 and LF6 were not able to grow on PDA plates containing 600 μg Zeocin or 200 μg G418.

Using the two basic vectors and three selectable markers six vectors were made (Table 4).

TABLE 4

The vector constructs made

| Basic vector | Marker | Construct | Basic vector | Marker | Construct |
|---|---|---|---|---|---|
| pUR5750 | Hpt | pURGHT2 | pCB301 | Hpt | pCGHT3 |
|  | Ble | pURGBT1 |  | Ble | pCGBT2 |
|  | NptII | pURNT3 |  | NptII | pCGNT13 | d) Transformation with the Six Newly Constructed Vectors

A mixture of conidia and ascospores from *M. ruber* strain LF5 was transformed with the six vectors as described before. After the cocultivation step the filters with the outgrowing conidia and ascospores were transferred to selective plates.

The selective plates contain YM-medium with 200 μM cefotaxime to kill the *Agrobacterium* cells and either 100 μg Hygromycin, or 200 μg Zeocin, or 200 μg Geneticin to select for transformants.

After approx. 12 days the first growing colonies became visible on the selective plates. Table 5 shows the score of the transformants.

TABLE 5

Transformants obtained from LF5 conidia.

| Vector | Marker | No. of |
|---|---|---|
| pURGH | Hpt | 7 |
| pURGB | Ble | 0* |
| pURGN | NptII | 1 |
| pCGHT | Hpt | 18 |
| pCGBT | Ble | 0* |
| pCGNT | NptII | 9 |

*General disperse growth, no specific colonies visible.

Colonies were transferred to PDA plates with appropriate antibiotics and after sufficient growth used as an inoculum for growth in liquid medium (YPD) containing the antibiotic. Mycelium was harvested after 4 days and DNA was isolated.

In order to establish the integration of the selectable marker gene in the genome from the *M. ruber* LF5 transformants two PCR analysis were performed on a number of transformants. The first analysis which will show the presence of the selectable marker in the isolated DNA is a PCR with primers specific for the marker genes. The second PCR analysis which excluded the presence of contaminating vector DNA, possibly coming from surviving *A. tumefaciens* bacteria, was performed with primers specific for the *A. tumefaciens* GPD (glyceraldehyde phosphate dehydrogenase) gene.

In conclusion it has been shown that Hpt and NptII vectors which have been constructed according to the cassette strategy are effective in transforming *M. ruber*. Using the smaller pCB301 based vector seems to result in more transformants than the pUR5750 based ones. PCR analysis shows integration of the selectable marker genes in the genome of *M. ruber* and also shows that *A. tumefaciens* bacteria have efficiently been killed by the Cefotaxim.

II. Transformation with a LDH Gene a) Vector Construction

For the introduction of at least one copy of the Bovine (*Bos taurus*) LDH gene in the genome of the *Monascus ruber* strains, the most straightforward approach is introducing a codon optimized Bovine LDH gene in the cassette as described hereabove. The promoter and terminator sequences driving the expression of the LDH gene will be the same has those driving the selectable marker gene.

For codon optimization we first analyzed the codon usage of *Monascus*. Since only two genes from *M. ruber* are available we compared the codon usage of *M. pilosus* and *M. purpureus* with the codon usage of the *M. ruber* genes. The three species are closely related and a great deal of similarity between the codon preference of the three *Monascus* species was found.

Figure 5:
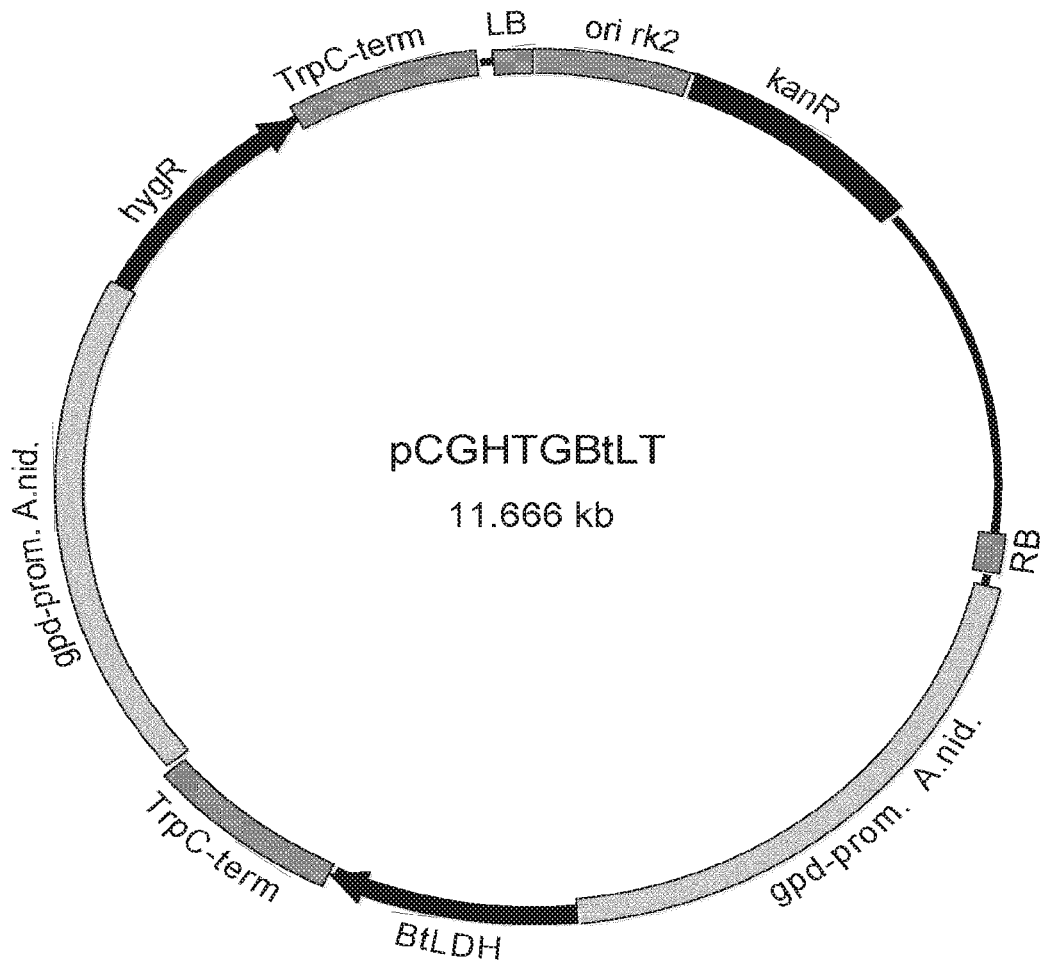
FIG. 5 illustrates transformation vector pCGHTGBtLT with the codon optimized (*Bos taurus* Bt) LDH gene, according to a particular embodiment of the invention.
Figure 6:
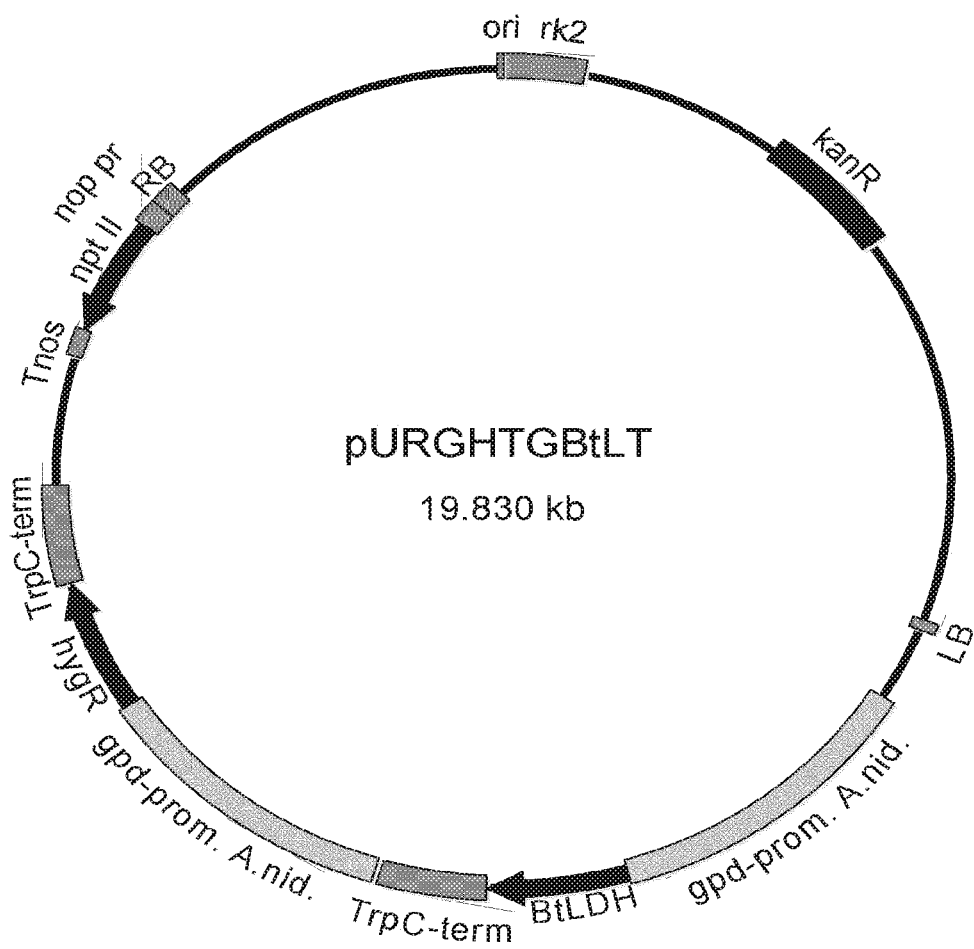
FIG. 6 illustrate transformation vector pURGHTGBtLT with the codon optimized (*Bos taurus* Bt) LDH gene based on the pUR5750 plasmid according to a particular embodiment of the invention.

Based on the codon usage we were able to design a optimized Bovine LDH gene for expression in the *M. ruber* strains selected (SEQ ID NO:1 and FIG. 4) and had such a gene synthesized by Genscript Corporation. After obtaining this gene it was cloned into both type of Hpt vectors constructed and tested. The cloning was performed according to the cassette strategy shown in FIG. 2 which has the advantage that the original vector is unchanged except for the insertion of the promoter-LDH-terminator cassette. This results in vectors pCGHTGBtLT based on the pCB301 plasmid (FIG. 5) and pURGHTGBtLT based on the pUR5750 plasmid (FIG. 6).

b) Cloning and Expression of the Bt-LDH Gene in *E. coli*.

In order to confirm the correct translation and the activity of the synthetic LDH gene used for transforming *M. ruber*, the gene was cloned in an *E. coli* expression vector. The expression vector used is the InVitrogen pBAD102 vector which will express the protein after Arabinose induction.

LDH was highly expressed in *E. coli* but was found to be partly soluble.

The soluble *E. coli* proteins were used to analyse the LDH enzyme activity.

The reaction catalyzed by the btLDH is:

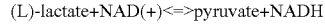

(L)-lactate+NAD(+)<=>pyruvate+NADH

In the activity assay an excess of pyruvate and NADH is added so the activity is reflected by the conversion of NADH to NAD which can spectrofotometrically be measured at 340 nM.

As a positive control LDH enzyme obtained from Sigma-Aldrich was used.

The reaction velocity was determined by a decrease in absorbance at 340 nm resulting from the oxidation of NADH. One unit causes the oxidation of one micromole of NADH per minute at 25° C. and pH 7.3, under the specified conditions.

0.2 M Tris•HCl buffer was prepared. The LDH enzyme was diluted prior to use to obtain a rate of 0.02-0.04 ΔA/min. in Tris buffer and kept cold.

A reaction mix of 2.8 mL Tris•HCl, 0.2 M pH 7.3 and 0.1 mL 6.6 mM NADH was prepared.

LDH activity was measured with and without substrate added, in order to monitor background NADH conversion.

Figure 7:
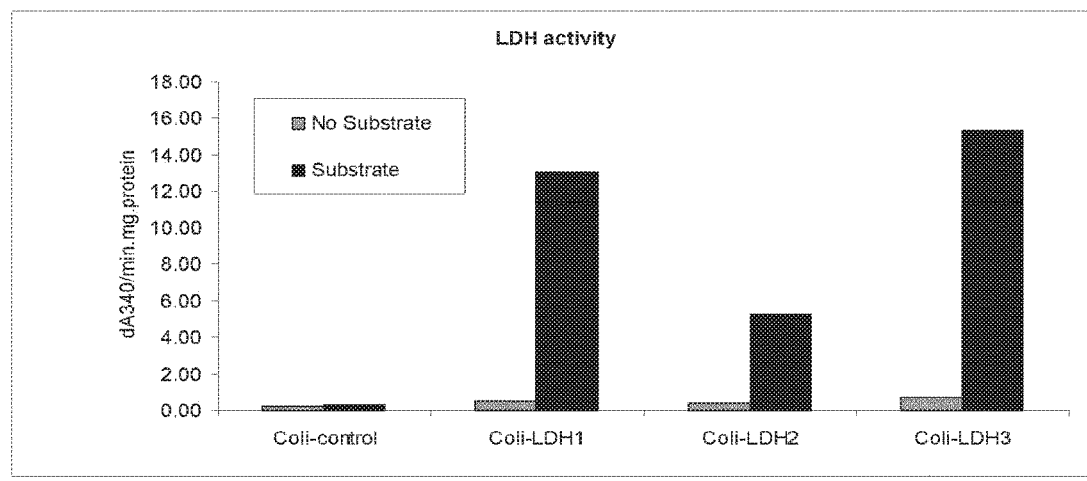
FIG. 7 illustrates LDH activity in *E. coli* protein extracts after expression of the synthetic LDH gene, according to a particular embodiment of the invention.

The analysis of the expression and activity of the synthetic LDH in *E. coli* shows that the synthetic gene encodes a protein of the correct Mw and with LDH activity. The glucose and lactose production by these *E coli* strains over time are shown in FIG. 7 ("*Coli*-LDH 1, 2, and 3" correspond to three independent *E. coli* extracts with the expressed synthetic LDH protein present; "*Coli*-control" is an *E. coli* extract expressing a different protein).

c) Transformation of *Monascus ruber* with the LDH Vectors.

A mixture of conidia and ascospores from *M. ruber* strains LF4, LF5 or LF6 was used for transformation with the LDH vectors pCGHTGBtLT and pURGHTGBtLT. So in total 6 transformations were performed. After applying the transformation procedure as described before and selection on hygromycin containing plates only three LF5 transformants were obtained.

One transformant resulted from the use of the pCGHTGBtLT vector (LF5-t1) and two from the pURGHTGBtLT vector (LF5t2, LF5-t5).

d) Analysis of *M. ruber* LF5-T1 and LF5-1-2-LDH Transformants

In a first experiment, two transformants LF5-T1 and LF5-T2 were analysed.

LF5-T1 was transformed with pCGHTGBtLT, and LF5-T2 with pURGHTGBtLT.

In order to analyze the LDH enzyme activity and possible L-lactate production the two transformants and the wt-LF5 strain were grown in S.c. medium+50 g/L glucose pH 6.0.

Medium and biomass samples were taken from individual cultures after 24, 48, and 72 hours of cultivation.

(i) Glucose Consumption and Lactate Production

Figure 8A:
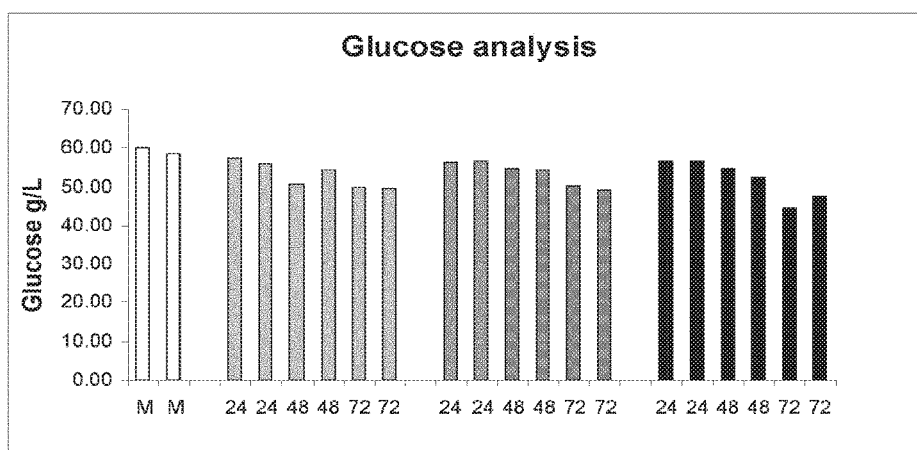
FIG. 8A illustrates glucose concentration in the media as determined by HPLC for transformants LF5-T1 and LF5-12 and untransformed *M. ruber* control LF5 according to particular embodiments of the invention.
Figure 8B:
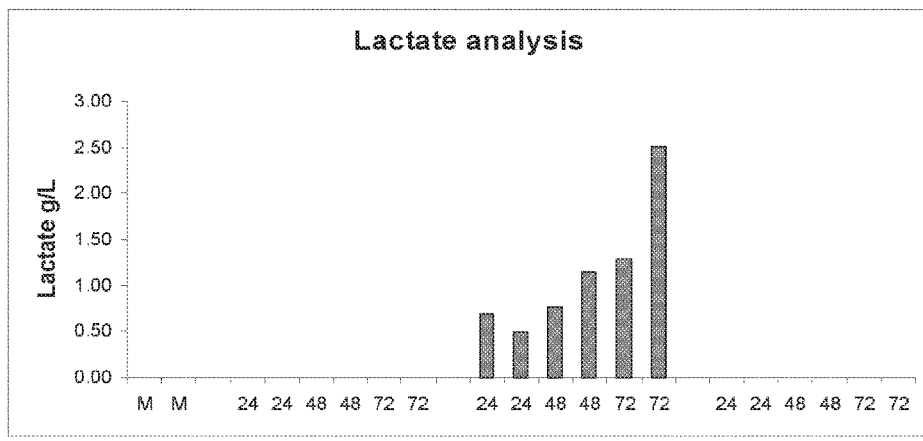
FIG. 8B Lactic acid concentrations in transformants LF5-T1 and LF5-T2 and untransformed *M. ruber* control LF5 according to particular embodiments of the invention.

FIGS. 8a and 8b clearly show glucose consumption in all cultures while in the medium from LF5-T2 lactic acid is detected increasing in concentration with time (the numbers 24, 48 and 72 indicate samples from two separate cultures grown for 24, 48 and 72 hours; "M" corresponds to medium). LF5-12 consumed approximately 8 g/L glucose and produced approximately 1.5 to 2 g/L of lactic acid, indicating a yield between 0.18 and 0.25 g/g was reached. The maximum theoretical yield is 1.00 g/g.

(ii) Enzymatic Analysis

Figure 9:
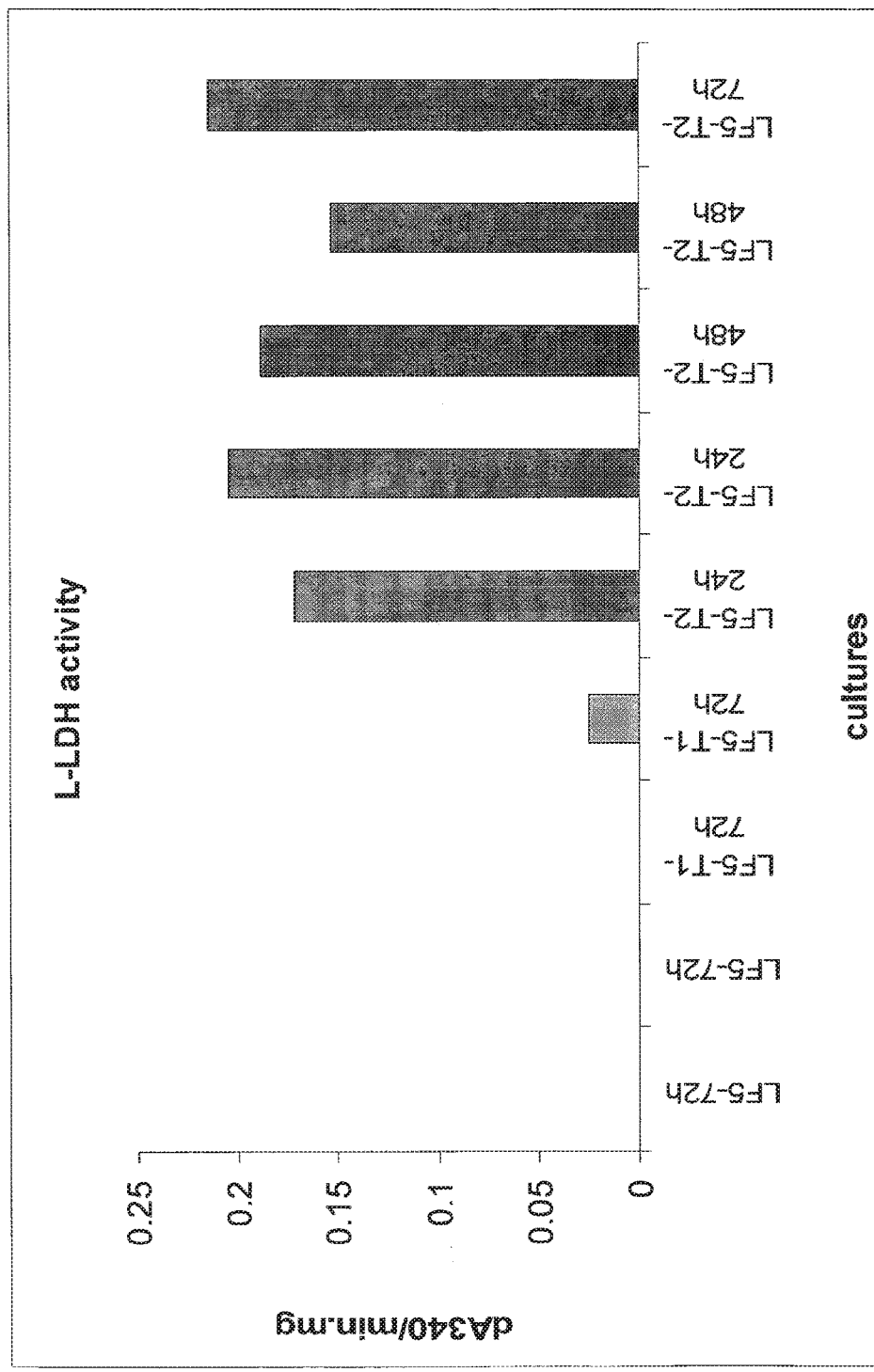
FIG. 9 illustrates the L-LDH enzyme activity in the biomass of the two transformants LF5-T1 and LF5-T2 and the untransformed *M. ruber* control LF5 according to particular embodiments of the invention.

Since the HPLC analysis does not discriminate between L- and D-lactic acid a number of samples was analyzed by an enzymatic method. A L-lactic acid analysis kit (Megazyme) confirmed the presence of L-lactic acid in the LF5-T2 samples (FIG. 9). The harvested biomass samples were frozen in liquid nitrogen and ground using a mortar and a pestle. The frozen powder was thawed in buffer (0.2 M Iris HCl, pH 7.3) and the protein was extracted by vortexing.

After centrifugation the supernatant was subjected to protein analysis and to an LDH-enzyme activity analysis as described in the previous paragraph.

This analysis clearly showed the presence of L-LDH activity in the LF5-T2 transformant, whereas no activity was found in the control (FIG. 9).

(iii) Southern Blot Analysis

Hybridization was performed using the LDH gene. Southern blot analysis confirms a single integration of the LDH gene in the genome of the *M. ruber* transformant t2, after growth in non selective medium. Transformant t1 was found not to contain the LDH gene. A second Southern analysis with the hygromycin gene shows integration of the hygromycin gene in both transformants. This indicates that in transformant t1, the gene cassettes, LDH and hygromycin between both borders was not completely integrated.

(iv) Conclusion

Using the transformation vectors constructed with a combination of a selectable marker and a synthetic LDH gene 27 *M. ruber* transformants were obtained. One transformant, LF5-T2 shows production of lactic acid when grown on glucose medium.

Lactic acid production, L-LDH activity and southern blots support the conclusion that we have inserted an L-LDH encoding heterologous gene in the genome of this *M. ruber* LF5-T2 transformant in such a way that it is expressed and metabolically active.

e) Analysis of *M. ruber* LF4-, LF5-, and LF6-LDH Transformants

Figure 10A:
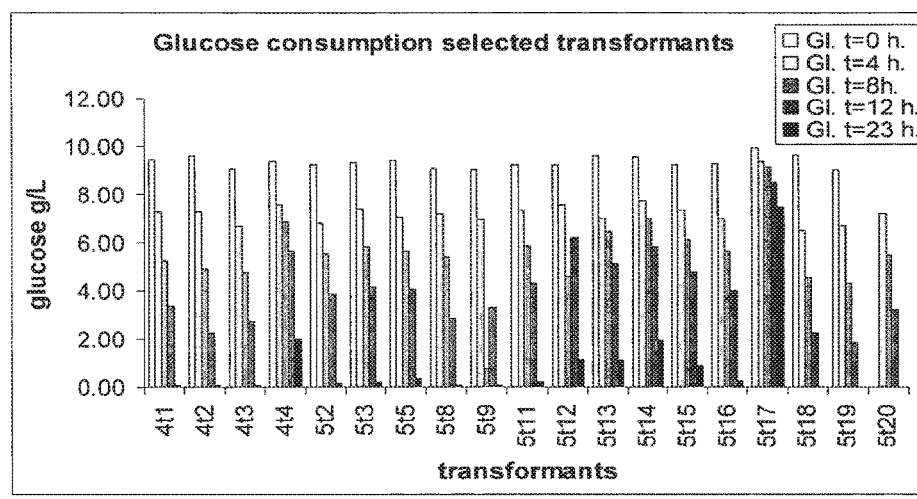
FIG. 10A illustrates the consumption of glucose by transformants of strains LF4 and LF5, according to particular embodiments of the invention.
Figure 10B:
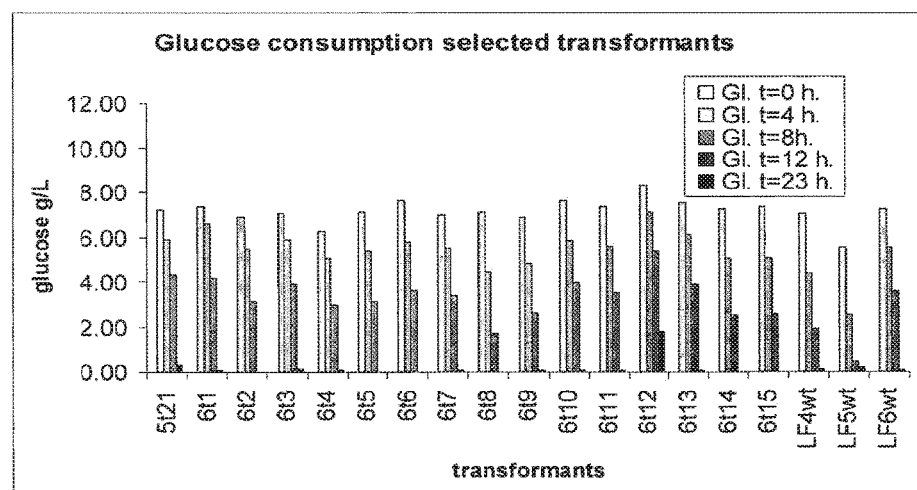
FIG. 10B illustrates the consumption of glucose by transformants of strains LF5 and LF6, according to particular embodiments of the invention, and wild type strains LF4, LF5, and LF6.
Figure 11A:
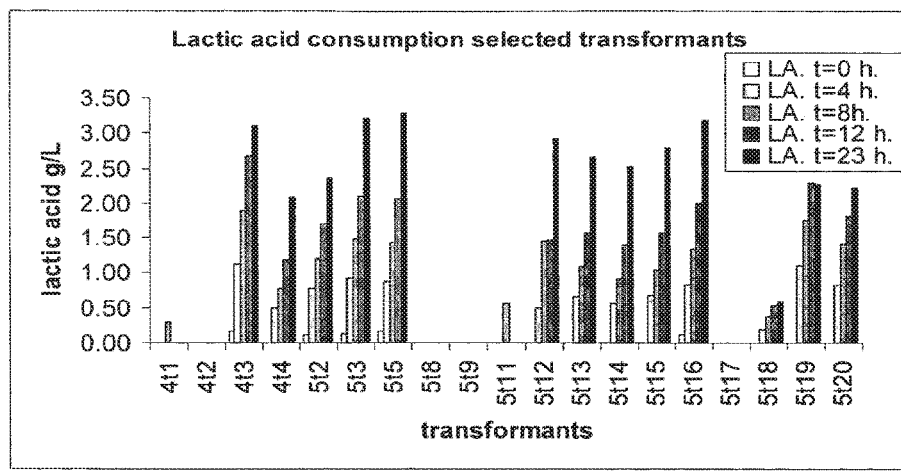
FIG. 11A illustrates the production of lactic acid by transformants of strains LF4 and LF5, according to particular embodiments of the invention.
Figure 11B:
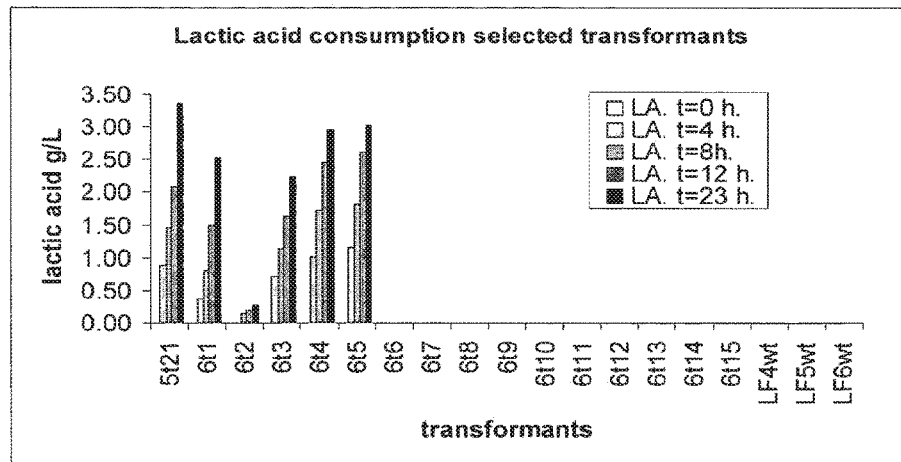
FIG. 11B illustrates the production of lactic acid by transformants of strains LF5 and LF6, according to particular embodiments of the invention, and by wild type strains LF4, LF5, and LF6.
Figure 12A:
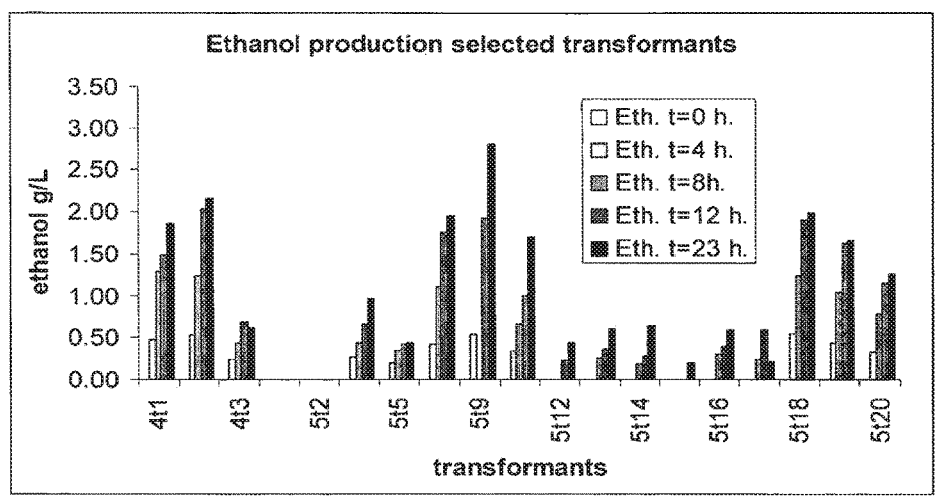
FIG. 12A illustrates production of ethanol by transformants of strains LF4 and LF5, precultured in 10 ml YEPD medium for 3 days.
Figure 12B:
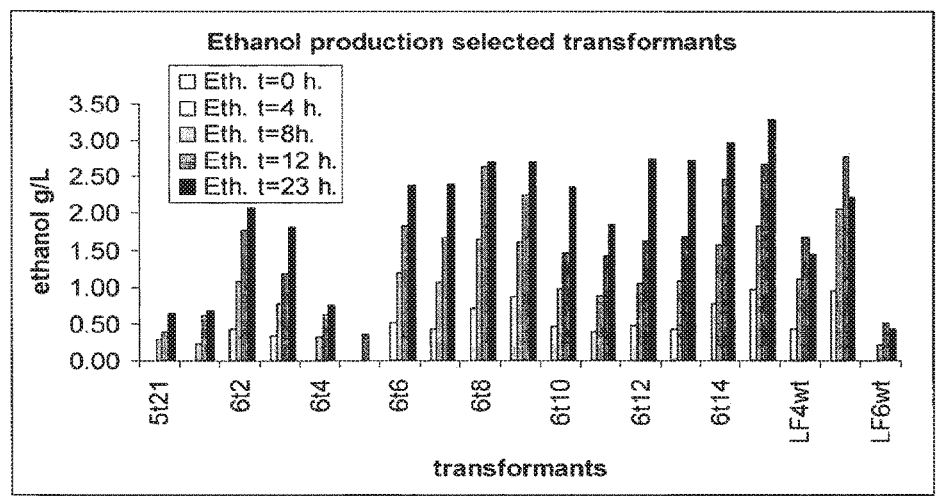
FIG. 12B illustrates production of ethanol by transformants of strains LF5 and LF6, and by wild type strains LF4, LF5, and LF6, precultured in 10 ml YEPD medium for 3 days.
Figure 13A:
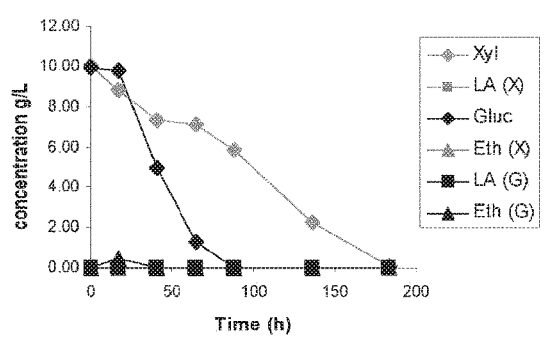
FIG. 13A illustrates the sugar (glucose or xylose) consumption and product (ethanol and lactic acid) formation by wild type LF4 under aerobic conditions.
Figure 13B:
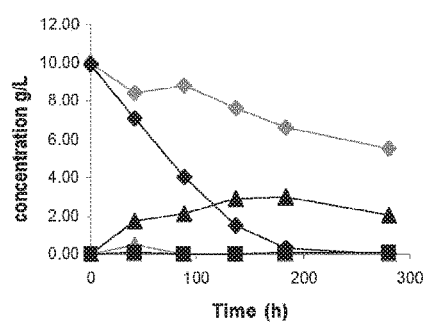
FIG. 13B illustrates the sugar (glucose or xylose) consumption and product (ethanol and lactic acid) formation by wild type LF4 under anaerobic conditions.
Figure 13C:
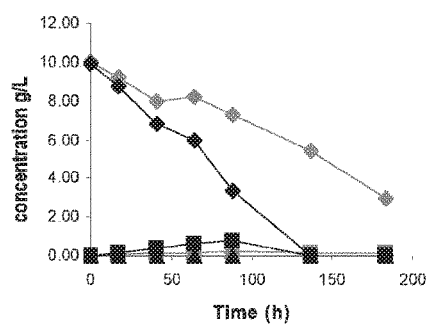
FIG. 13C illustrates the sugar (glucose or xylose) consumption and product (ethanol and lactic acid) formation by transformant 4t3 under aerobic conditions.
Figure 13D:
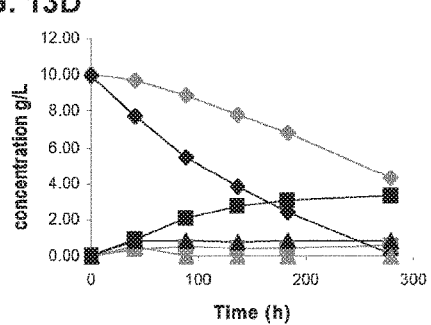
FIG. 13D illustrates the sugar (glucose or xylose) consumption and product (ethanol and lactic acid) formation by transformant 4t3 under anaerobic conditions.
Figure 13E:
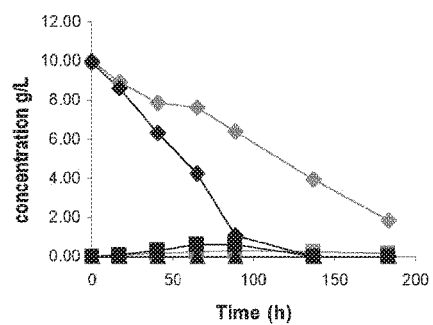
FIG. 13E illustrates the sugar (glucose or xylose) consumption and product (ethanol and lactic acid) formation by transformant 4t4 under aerobic conditions.
Figure 13F:
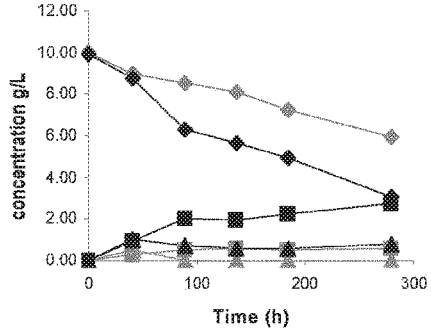
FIG. 13F illustrates the sugar (glucose or xylose) consumption and product (ethanol and lactic acid) formation by transformant 4t4 under anaerobic conditions.

In a next experiment, a total of 35 transformants were analyzed, i.e. 4 of LF4, 16 of LF5 and 15 of LF6. Strains were precultured in 10 ml YEPD medium for 3 days. Biomass was washed in Sc medium with 10 g/L glucose at pH 2.8 and was cultivated in 15 ml of Sc medium with same composition. The glucose consumption by the strains in illustrated in FIG. 10. Nineteen (54%) of these transformants, i.e. two derived from LF4, twelve derived from from LF5 and five derived from LF6, produced lactic acid from glucose (FIG. 10). In the positive experiments, varying amounts of lactic acid were found, ranging from 0.5 to 3.3 g/L, corresponding to 5-33% of the maximal theoretical yield (FIG. 11). Ethanol was formed as byproduct, its concentration inversely related to the lactic acid concentration (FIG. 12).

Two transformants of each strain were selected (4t3, 4t4, 5t2, 5t21, 6t4, 6t5), the one with the highest lactic acid production and one with the lowest ethanol production. The strains were subsequently cultivated in shake flasks (on either glucose or xylose (both 10 g/L)), under two different aeration conditions: aerobic and severely oxygen limited. Under aerobic conditions, strains were precultured in 100 ml shake flasks on 10 ml YEPD for three days. The cultures were then washed twice with 25 ml Sc medium, at pH 2.8. Biomass was homogenized in 10 ml of the same medium using a triangular magnetic stirring rod. 750 microliters were used to inoculate 15 ml of Sc medium, pH 2.8, containing 10 g/L of glucose or xylose (FIGS. 13-15).

Alternatively, under severely oxygen limited conditions, cultures were performed in bottles closed with an aluminium capped butyl rubber stopper equiped with bicycle tube valves to create severely oxygen limited, almost anaerobic conditions. Precultured in 100 ml shake flasks on 10 ml YEPD during 3 days. The cultures were then washed twice with 25 ml S.c medium, at pH 2.8. Biomass was homogenized in 10 ml of same medium using a triangular magnetic stirring rod. 750 microliters were used to inoculate 15 ml of Sc medium, pH 2.8, containing 10 g/L of glucose or xylose.

In the aerobic cultures (left panels of FIGS. 13-15) some lactic acid was produced (approximately 0.5-1 g/L) from glucose. The lactic acid was consumed after the glucose was fully consumed. No ethanol was formed. Under severely oxygen limited conditions (right panels of FIGS. 13-15) the lactic acid concentration was between 2.0 and 3.3 g/L, and ethanol was produced at concentrations varying between 0.5 and 1.0 g/L.

Example 3: Further Improvement of Lactic Acid Yield by Eliminating Ethanol Production a) Identification of the Pyruvate Decarboxylase Genes Using Sequence Homology In order to further improve lactic acid yield a gene knock-out system was envisaged to reduce the production of products other than lactic acid on the one hand and to reduce the metabolism of lactic acid by *Monascus* on the other hand. More particularly, in order to avoid the production of alcohol, a knock-out system was envisaged based on genes encoding *M. ruber* homologues of the *S. cerevisiae* PDC1 gene encoding pyruvate decarboxylase (EC 4.1.1.1).

*M. ruber* produces ethanol under oxygen-limited conditions. Since both ethanol and lactic acid are produced from pyruvate, the production of ethanol should be prevented since it decreases the yield of lactic acid. Using BLAST with the *S. cerevisiae* PDC1 gene as the query we found several homologues in the *Aspergillus niger* genome which could represent a PDC encoding gene. *A. niger* was used because of its close relationship to *Monascus*. Based on these sequences we designed degenerated PCR primers in order to be able to clone part of a *M. ruber* PDC.

RT-PCR on RNA from *M. ruber* strain LF6 resulted in two 1.3 kB DNA fragments which were cloned in a plasmid. Sequencing of these cloned PCR fragments confirmed the presence of two open reading frames with high homology to the *Aspergillus niger* PDC homologues and sufficient homology to the *S. cerevisiae* PDC1 gene to conclude that we have cloned two PDC1 analogues of *Monascus ruber*.

The open reading frame for the *M. ruber* PDC genes PDC1 and PDC2 is provided as SEQ ID NO:3 and 4 (and FIGS. 16 and 17).

b) Construction of a Gene Knock-Out Vector.

i) Knock-Out of PDC Genes

Figure 18:
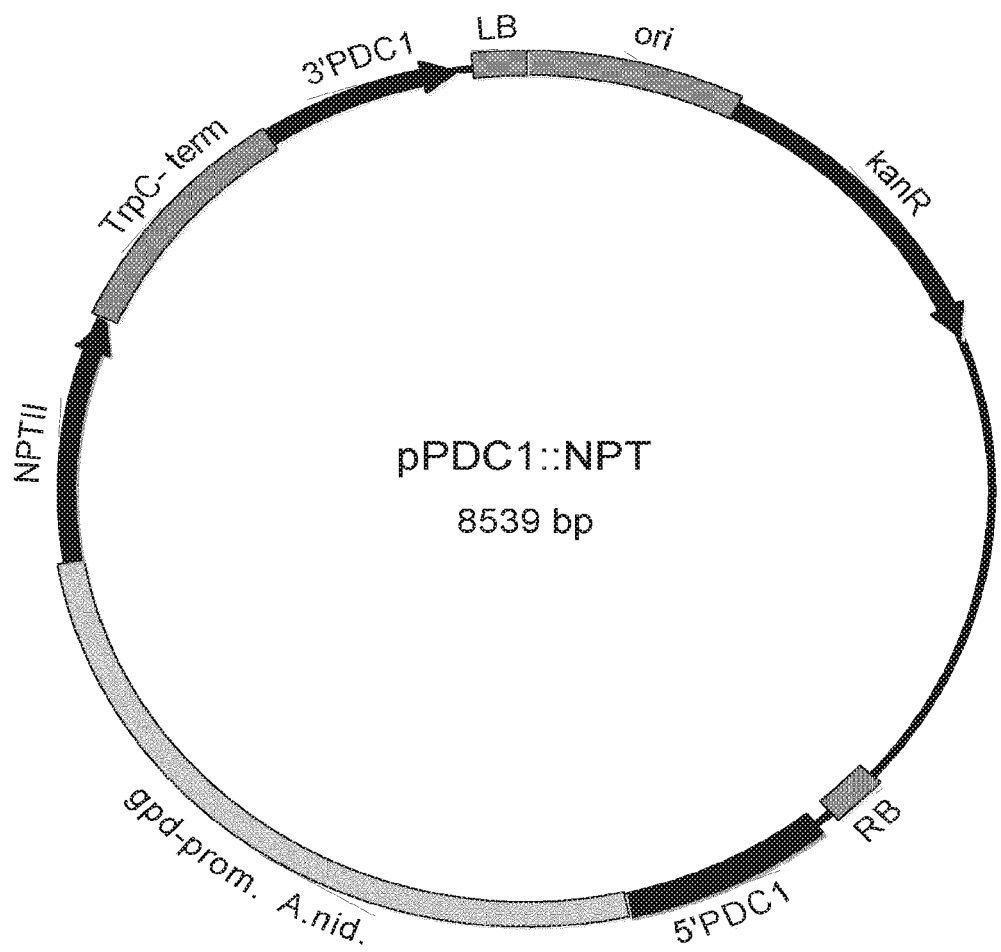
FIG. 18 illustrates an example of a transformation vector which can be used for the disruption of PDC1 of *Monascus* strains using geneticin selection according to particular embodiments of the invention.
Figure 19:
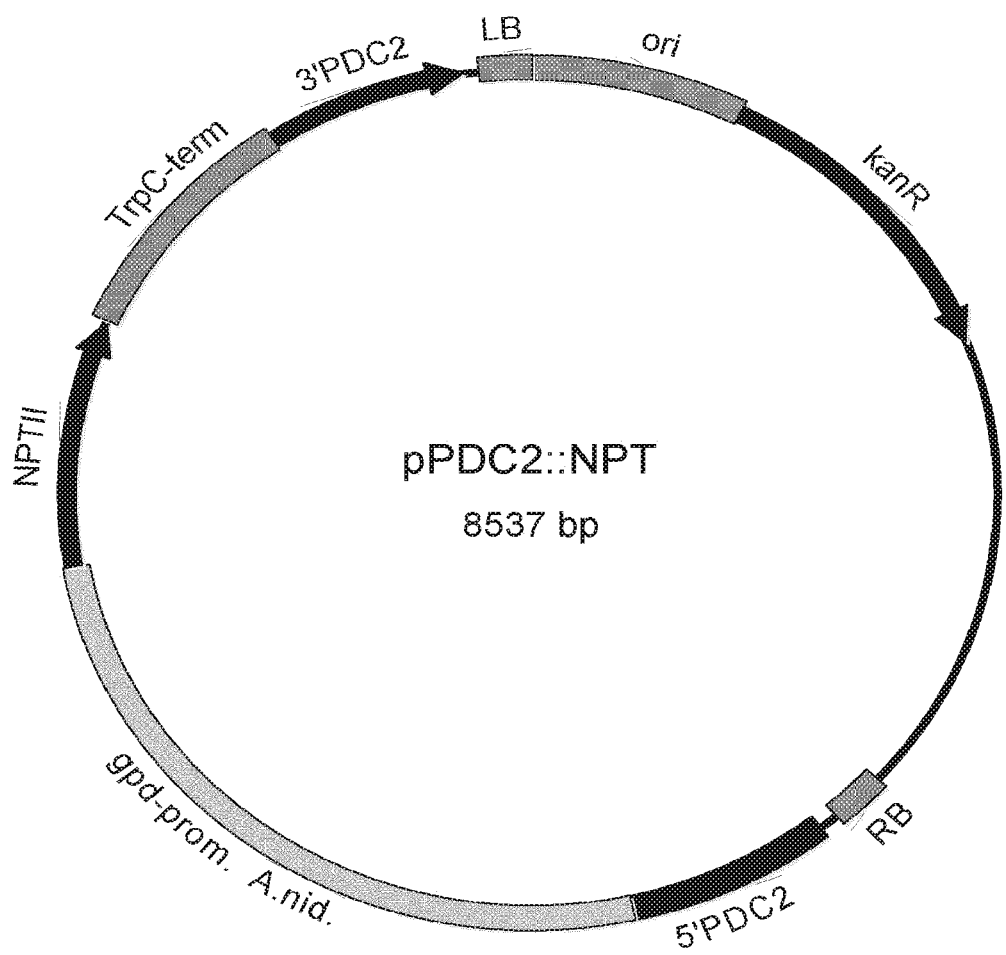
FIG. 19 illustrates an example of a transformation vector which can be used for the disruption of PDC2 of *Monascus* strains using geneticin selection according to particular embodiments of the invention.
Figure 20:
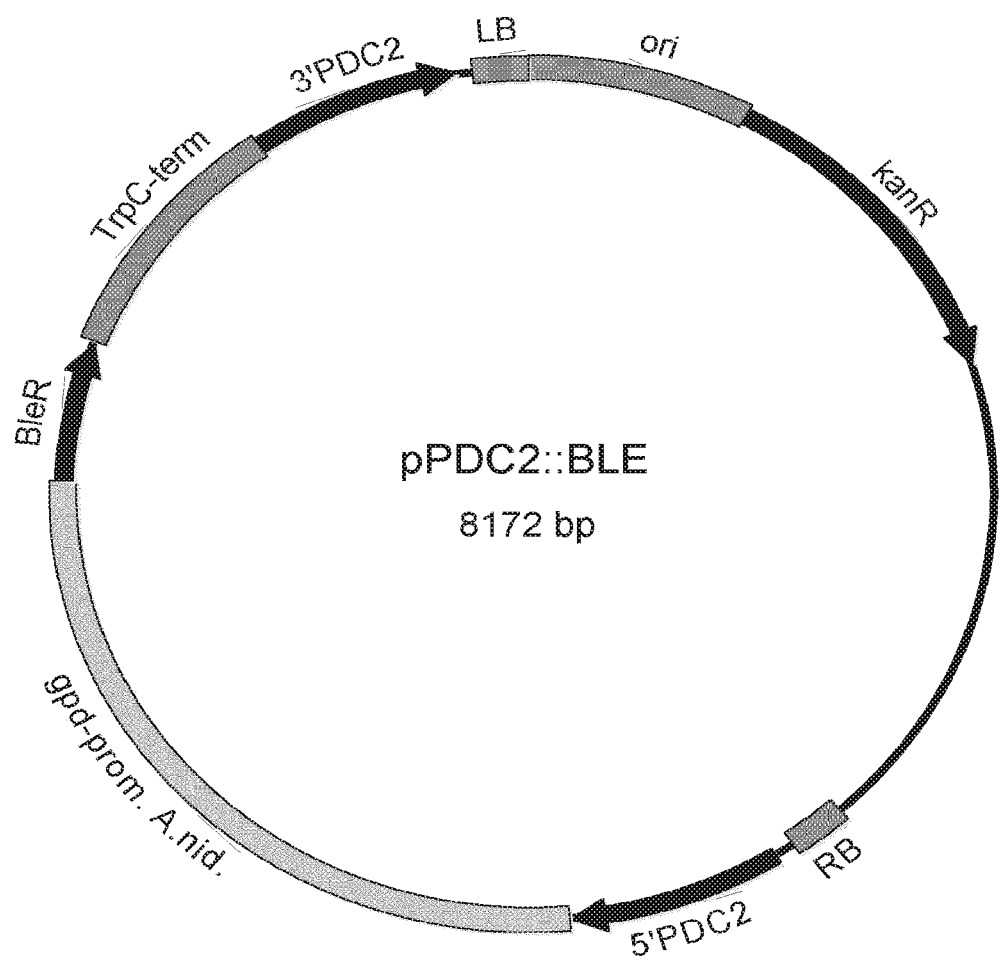
FIG. 20 illustrates an example of a transformation vector which can be used for the disruption of PDC2 of *Monascus* strains using zeocin selection according to particular embodiments of the invention.

Using PCR, the 5' and 3' halves of the PDC1 and PDC2 genes were isolated and suitable restriction sites are added to the ends. The 5' halves are then cloned 5' of the promoter-marker-terminator cassette of vectors pCGNT1 and pCGBT2 (and 3' of the Right Border sequence). These vectors are identical to the previously described vector pCGHT3, except that the NPTII and BLE genes are used as selectable markers instead of the HPT gene. Likewise, the corresponding 3' halves are cloned 3' of the promoter-marker-terminator cassette (and 5' of the Right Border sequence). In this manner, three vectors are generated:

1. pPDC1::NPT for disruption of PDCI using geneticin selection (FIG. 18)
2. pPDC2::NPT for disruption of PDC2 using geneticin selection (FIG. 19)
3. pPDC2::BLE for disruption of PDC2 using zeocin selection (FIG. 20)

Figure 21:
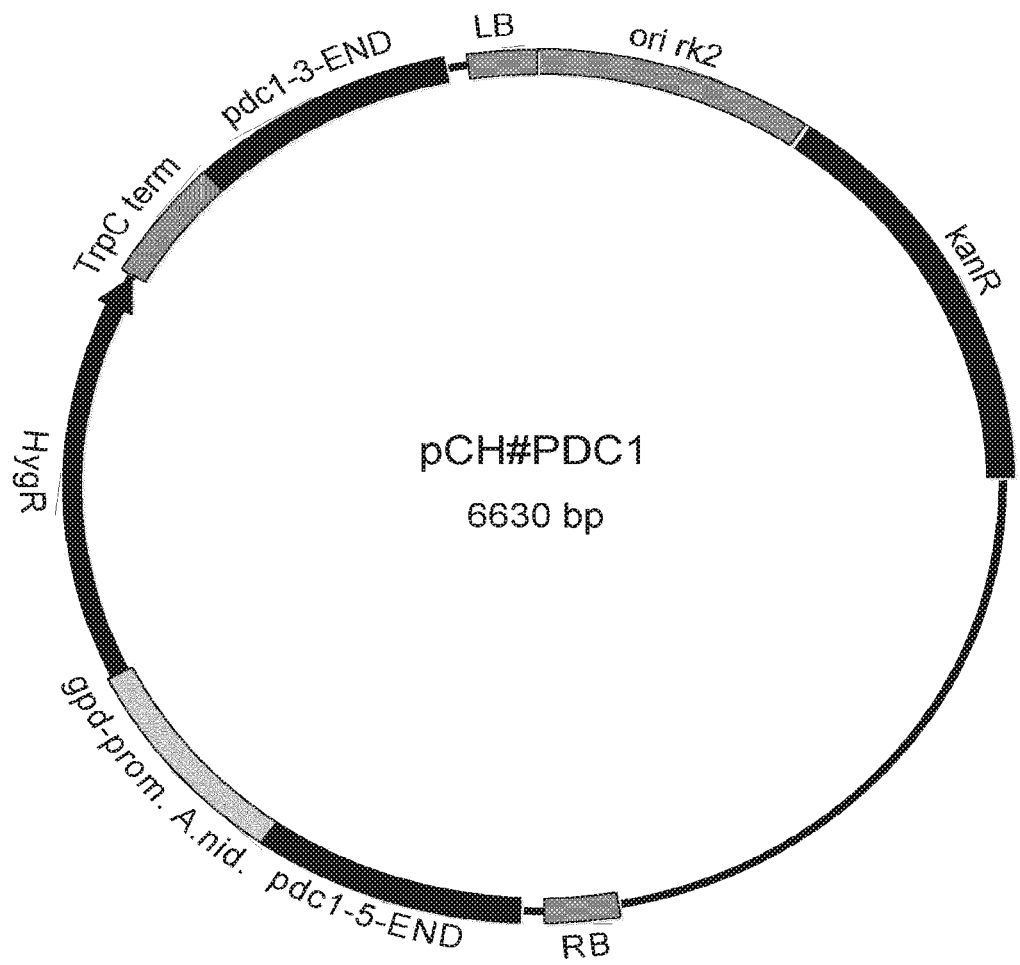
FIG. 21 provides a schematic representation of vector pCH#PDC1 used to disrupt the PDC1 gene.
Figure 22:
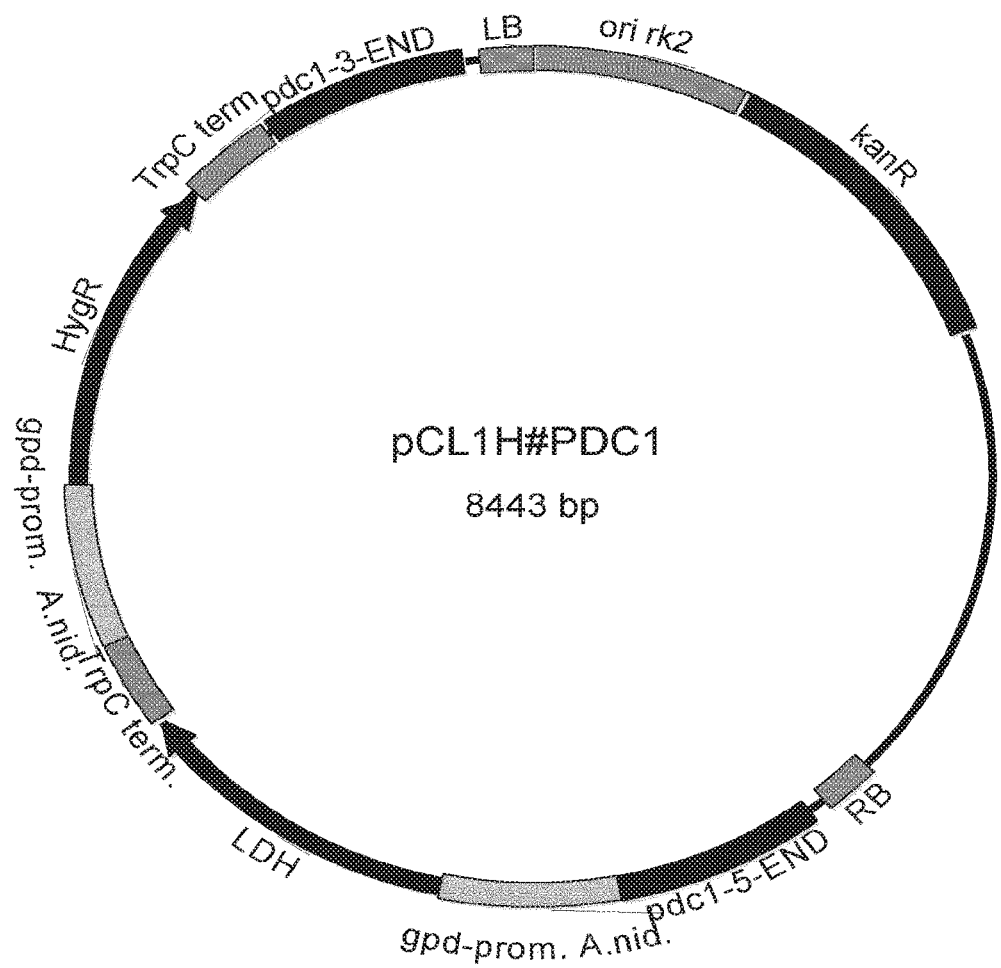
FIG. 22 provides a schematic representation of vector pCL1H#PDC1 used to disrupt the PDC1 gene and insert the LDH gene simultaneously.
Figure 23:
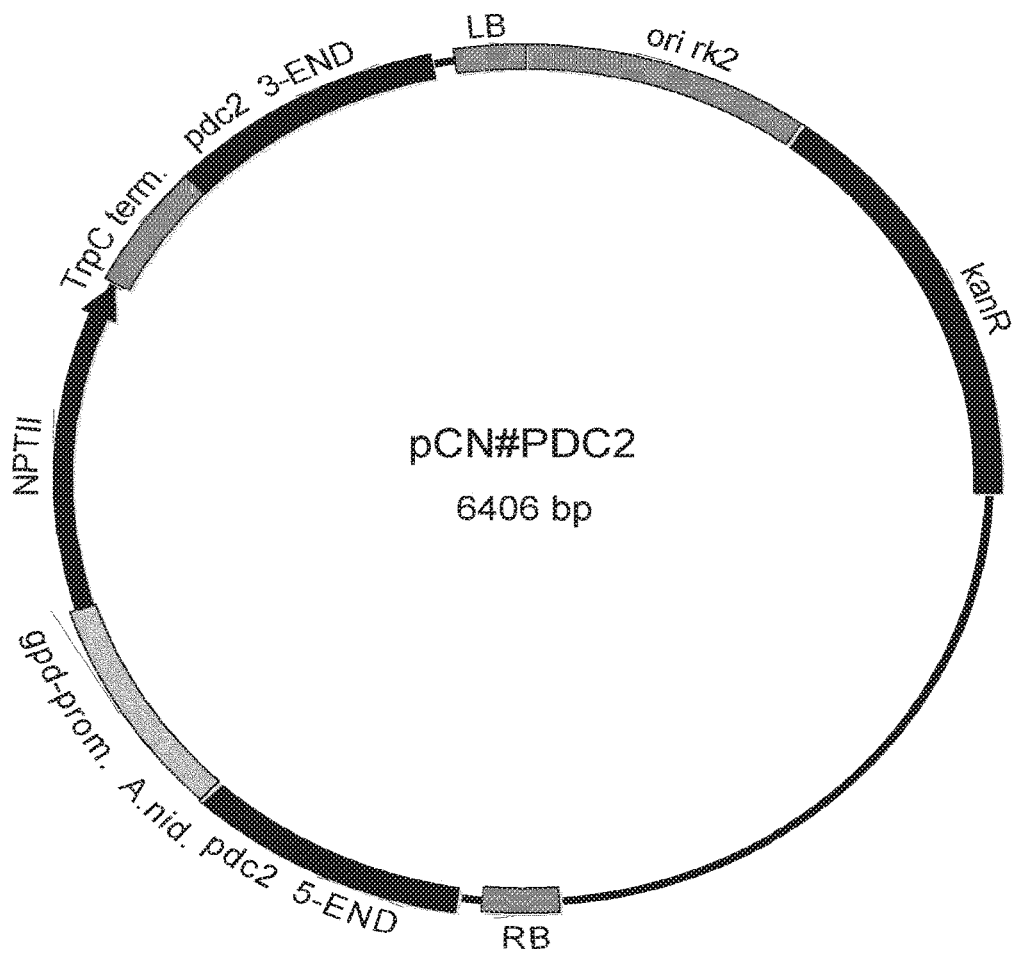
FIG. 23 provides a schematic representation of vector pCN#PDC2 used to disrupt the PDC2 gene in a PDC1-LDH-F transformant.

These vectors are used in a previously constructed PDC1::NPT disruptant ii) Combined Knock Out and Gene Insertion Vectors were constructed to enable simultaneous disruption of a target gene and introduction of another gene. In order to minimize unwanted recombination in a second round of transformation due to the presence of long stretches of DNA in the vector and in order to increase the cloning efficiency during vector construction the size of the promoter and terminator sequences were reduced in the new vectors. Using PCR the size of the GPD promoter was reduced from 2208 bp to 538 bp and the TrpC terminator was reduced from 763 bp to 278 bp. These are vector pCH#PDCI and vector pCL1H#PDC1 (see FIGS. 21 and 22). The pCH#PDC1 vector is used for the disruption of PDC1 using hygromycin selection. The pCL1H#PDCI vector is used for the disruption of PDC1 and introduction of LDH using hygromycin selection. Transformants resulting from these vectors have a disrupted PDC1 gene and a disrupted PDC1 gene+an inserted LDH gene respectively. The vector pCN#PDC2 was constructed to disrupt the PDC2 gene using geneticin selection (FIG. 23).

c) Generating Knock-Out Transformants i) Knock-Out of PDC Genes

Spores obtained from LF6 LDH transformant t4 and t5 are used in transformation experiments with the knock out vectors pPDC1::NPT or pPDC2::NPT. After selection on G418 (geneticin) each combination of strain and vector results in 50-80 geneticin resistant colonies. By means of PCR with gene specific primers the DNA of 40 transformants (20 LF6t4+pPDC2::NPT transformants and 20 LF6t5+pPDC2::NPT transformants) are tested for the presence of the NPTII gene and for the disruption of the PDC2 gene. Disruption of the PDC2 gene with the knock out vector is observed.

ii) Combined Knock Out and Gene Insertion

The vectors pCH#PDC1 and pCL1H#PDC1 were used to transform the spores, collected from the wild type strain LF6 at 40° C., according to our standard procedure. After 10 days of growth on selective plates containing hygromycin growing colonies were observed and 20 of them were transferred to new hygromycin containing plates and tested by PCR for PDC1 gene knock out.

PCR analysis shows that in 1 out the 20 transformants from pCH#PDC1 and in 3 out of 20 transformants from pCL1#PDC1 the PDC1 gene has been disrupted (Table 6).

TABLE 6

Number of transformant per construct

| construct | Colonies total | Colonies | PDC1 knockout |
|---|---|---|---|
| pCH#PDC1 | 53 | 20 | 1 |
| pCL1H#PDC | 97 | 20 | 3 |

The vector pCN#PDC2 was used to transform spores from a PDC1 knock out strain from transformation round 1. After 10 days of growth on selective plates containing geneticin growing several colonies were observed and 40 of them were transferred to new geneticin containing plates and tested by PCR for PDC2 gene knock out.

Strain LF6KL19 was confirmed to be a double knockout of PDC1 and PDC2 and contains the recombinant LDH gene.

d) Analysis of Transformants

Strain LF6KL19 was precultivated in 300 ml Sc medium containing 50 g/l glucose and 1 g/l Junlon in a 2 L erlenmeyer at pH 2.8. The initial spore concentration was 1×105 spores. The incubation temperature was 30 or 35° C. and agitation speed was set at 75 rpm. At 30° C. 16.1 g/l glucose was consumed and 14.4 g/l lactic acid was produced, at 35 18.8 g/l of glucose was consumed and 18.6 g/l lactic acid was produced, indicating the actual yield was between 0.9 and 1.0 g/g. Under these conditions also the highest productivities were obtained: 0.15 g/l/h.

e) Genome and Transcriptome Analysis

The genome of M. ruber LF6 and the transcriptomes of M. ruber LF6 and M. ruber LF6KL19 (double PDC knock-out, introduced copy of bovine LDH), growing on different growth substrates, were sequenced and the relevant genes involved in alcohol production were identified on the genome by an automated annotation procedure. The RNA sequence data were used to improve the architecture of these genes. Many putative genes that are involved in the formation of ethanol were identified on the genome: 7 for pyruvate decarboxylases (PDCs) and 12 for alcohol dehydrogenases. 3 putative PDC genes were adjacent to each other in the genome, Analysis of the RNA sequence data showed that these 3 putative PDC genes belong to one single gene. The PDC2 product (SEQ ID NO:2) was identical to part of the translated sequence of this gene.

The PDC1 product was identical to part of the putative PDC gene product of Mona10180. Both genes encoding PDC1 and PDC2 were highly expressed under all circumstances. Besides these, also another PDC gene (Mona07809 or PDC4, SEQ ID NO: 5, FIG. 24) was transcribed under all circumstances and can be eliminated from the genome of M. ruber to reduce the production of ethanol.

Example 4: Further Improvement of Lactic Acid Yield by Eliminating of Endogenous Lactic Acid Metabolism a) Cyt-LDH Activity Analysis in M. ruber From literature it is known that in fungi and yeasts lactic acid is metabolized by a (cytochrome)L-lactate dehydrogenase. Therefore we first analyzed M. ruber strains grown on lactic acid for this enzyme activity.

M. ruber strains were grown on 2% yeast extract, 1')/0 peptone medium supplemented with 5% glucose or with 2% lactic acid as carbon source. As a control S. cerevisiae was grown under the same conditions (Lodi and Guiard, 1991). Biomass was harvested after 24 h of growth. The harvested biomass samples were frozen in liquid nitrogen and ground using a mortar and a pestle. The frozen powder was thawed in buffer (0.067 M sodium phosphate, pH 7.4 with 0.001 M EDTA) and the protein extracted by vortexing. After centrifugation the supernatant was subjected to protein analysis and to cyt-LDH-enzyme activity analysis. The rate of reduction of potassium ferricyanide is determined spectrophotometrically at 420 nm. Prior to assay, the enzyme was dissolved in 0.067 M phosphate buffer, pH 7.4 with 0.001 M EDTA to obtain a rate of 0.02-0.04 ΔA/minute. A mix of 2.0 ml of 0.1 M sodium pyrophosphate, 0.5 ml of 0.5 M DL sodium lactate, 0.3 ml of 0.01 M EDTA, and 0.1 ml of potassium ferricyanide was prepared and pipetted into a micro-titer plate. 10-20 µl of appropriately diluted sample was added and the ΔA420/m in was recorded.

Figure 25:
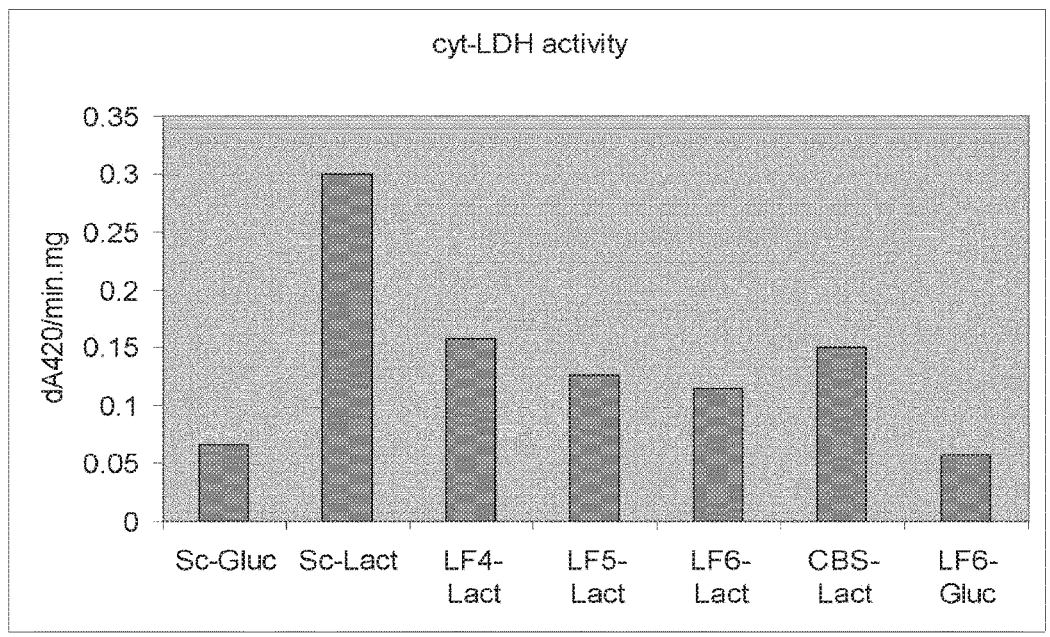
FIG. 25 illustrates Cyt-LDH activity in protein extracts from *S. cerevisiae* (Sc) and *Monascus* strains LF4, LF5, LF6, and the CBS strain, according to particular embodiments of the invention.

FIG. 25 shows the cyt-LDH activity in the protein samples. "Glue means grown in medium with glucose and "Lact" means grown in medium with L-lactic acid as a carbon source. Cyt-LDH activity is present in all tested M. ruber strains and is induced by growth on L-lactic acid as a carbon source.

b) Isolation of M. ruber Homologues of the CYB2 Gene Based on Sequence Homology

Using BLAST with the S. cerevisiae CYB2 gene as the query we found several homologues in the Aspergillus niger genome which could represent a cyt-LDH encoding gene. A. niger was used because of its close relationship to Monascus. Based on these sequences we designed degenerated PCR primers in order to be able to clone part of a M. ruber cyt-LDH.

PCR on genomic DNA from M. ruber strain LF6 resulted in a 1 kB DNA fragment which was cloned in a plasmid. Sequencing of this cloned PCR fragment confirmed the presence of an open reading frame with high homology to the Aspergillus niger CYB2 homologues and sufficient homology to the S. cerevisiae CYB2 gene to conclude that we have cloned a CYB2 analogue of Monascus ruber. The open reading frame for M. ruber CYB2 gene is provided as SEQ ID NO:2 and FIG. 26; a putative intron in the genomic sequence is indicated by small letters.

c) Genome and Transcriptome Analysis of Lactic Acid Metabolism

The genome of *M. ruber* LF6 and the transcriptomes of *M. ruber* LF6 and *M. tuber* KL19 (double PDC knock-out, introduced copy of bovine LDH), growing on different growth substrates, were sequenced and the relevant genes involved in lactic acid metabolism were identified on the genome by an automated annotation procedure. The RNA sequence data were used to improve the architecture of these genes. Several genes encoding lactic acid dehydrogenases were predicted for both isomers of lactic acid. For L-lactic acid, 4 cytochrome dependent LDH's were predicted, i.e. Mona 02475 (partly corresponding to SEQ ID NO:2), Mona 00569, Mona05565 en Mona06119. As Mona00569 was found to be the most active and was highly up regulated in the presence of lactic acid, this is the most obvious candidate for elimination. The sequence of this gene is given in SEQ ID No: 6 (FIG. 27).

*M. ruber* was also found to contain several putative genes for cytochrome dependent LDH's that use D-lactic acid as a substrate. Again, one gene (Mona05697) was the most active gene. Since expression of Mona05697 will only lead to consumption of the undesired D-isomer of lactic acid, it may be desirable but it is probably not necessary to eliminate this gene.

The invention claimed is:

1. A method of producing a composition comprising lactic acid, the method comprising:
(i) providing a *Monascus* micro-organism that is tolerant to organic acid at a concentration of at least 50 g/L and a pH of less than 5.0 and has been genetically modified for increased production of a lactic acid by the introduction of an exogenous lactate dehydrogenase (LDH) gene; and
(ii) culturing the micro-organism in a medium having a pH less than 1.5 units above the pKa value of lactic acid in the presence of hexose, pentose, or a combination thereof, as the sole carbon source.

2. The method of claim 1, wherein the lactic acid is L-lactic acid.

3. The method of claim 1, further comprising recovering the lactic acid from the medium.

4. The method of claim 1, wherein the micro-organism has been further genetically modified to delete or inactivate an endogenous LDH gene.

5. The method of claim 1, wherein the micro-organism has been further genetically modified to delete or inactivate a PDC1, PDC2, or PDC4 gene.

6. The method of claim 1, wherein: the micro-organism has been genetically modified to delete or inactivate a gene encoding pyruvate decarboxylase, fumarate reductase, alcohol dehydrogenase, acetaldehyde dehydrogenase, phosphoenolpyruvate carboxylase, D-lactate dehydrogenase, L-lactate dehydrogenase, or lactate 2-monooxygenase.

7. The method of claim 6, wherein the micro-organism has been genetically modified to delete or inactivate a gene encoding pyruvate decarboxylase, D-lactate dehydrogenase, or L-lactate dehydrogenase.

8. The method of claim 1, wherein the lactic acid is produced at a yield of at least 0.5 g/L.

9. The method of claim 8, wherein the yield is at least 2 g/L.

* * * * *

SEQUENCE LISTING

```
<160> NUMBER OF SEQ ID NOS: 6

<210> SEQ ID NO 1
<211> LENGTH: 999
<212> TYPE: DNA
<213> ORGANISM: Artificial Sequence
<220> FEATURE:
<223> OTHER INFORMATION: Codon optimized bovine LDH sequence
<220> FEATURE:
<221> NAME/KEY: Intron
<222> LOCATION: (503)..(566)

<400> SEQUENCE: 1
atggcaaccc tgaaggacca gcttatccaa aacctgctca aggaagaaca cgtcccccaa      60
aacaagatta ctatcgtcgg agtcggtgcc gttggaatgg cctgcgctat ctccattctg     120
atgaaggacc tcgcagatga ggtggcgctc gtcgacgtta tggaggataa gctcaagggt     180
gaaatgatgg accttcagca tggatcgctt ttcttgcgca cacccaagat cgtcagcggc     240
aaggattaca acgttacagc aaattcccgc cttgtgatca ttactgcagg cgcgcgtcag     300
caagagggtg aatcgagact gaacctcgtc caaaggaacg ttaatatctt caagttcatc     360
atccccaaca ttgtcaagta ctccccaaat tgtaagctgc tcgtcgtttc taatccggtt     420
gacatcctca cttatgtggc ctggaagatt tctggcttcc ctaagaaccg agttatcggc     480
tcgggttgca atcttgatag cgctcgattt cggtatctta tgggagagag attgggcgtc     540
catcccctgt cctgtcacgg ctggatcttg ggagaacacg gcgactcctc tgtgccagtc     600
tggtcgggtg tcaacgtggc cggagtcagc cttaagaatt tgcatccgga gttgggcacc     660
gacgccgata aggaacagtg gaaggctgtc cacaagcaag tggtcgactc cgcatacgag     720
gttatcaagc tgaagggata tacctcctgg gcgattggcc tctctgtggc cgatcttgct     780
gaaagcatca tgaagaactt cgccgtgtc catcctatct ccacgatgat taagggtctg     840
tacggaatta aggaagacgt gttttttgtct gtcccctgca tcctgggcca gaatggtatt     900
tcggatgttg tgaaggtcac cctcacgcac gaggaagagg cttgcttgaa gaagtcggcg     960
gacactctct ggggcatcca aaaggaactc caattttaa                             999

<210> SEQ ID NO 2
<211> LENGTH: 1015
<212> TYPE: DNA
<213> ORGANISM: Monascus ruber
<220> FEATURE:
<221> NAME/KEY: Intron
<222> LOCATION: (503)..(566)

<400> SEQUENCE: 2
aagtatgcgg ggcaggatgc cacaaaggcc tattctgaag ttcacactcc gagccttatc      60
```

```
aaatggaatt tatccccaga caagctcaag ggcactctcg gccaatccac tattgacgat    120
gaatggatga aaccaccgcc aaatgagagc gacaaagttg ttttagagaa cgagaaaccg    180
ccgctgcata tgctgataaa ctcgcacgat ttcgaagtcg tagcttccaa gactgcaagt    240
aagaagacct gggccttcta ttccagcgct gcaacggacc tcatcacccg tgatgccaat    300
aagtcatgct ttgaccggat atggttccga ccccgggtac tgaggaatgt gcgtaccgtc    360
aaaacgcgca cgaagatcct cggggttgac agcagtctcc cacttttcgt gagtccagca    420
gctatggcta agctcattca cccagatggt gagtgtgcca tagcaagggc atgtgcaaat    480
aagggtatca ttcaaggtgt acgttcattg cagattcgaa cacttcccgt tctagttgca    540
accttcttaa catcaatgtc ggataggtgt cgaataactc atcattccca atcgaagagc    600
tccgggaggc ggcaccgtct ggaaattta tttccagtt atatgtgaat cgggatcgag    660
agaaatctgc ggaactactc cgcaggtgct cagctaaccc gaacatcaag gccatcttcg    720
tgaccgttga cgcagcctgg cccggtaaac gtgaggcaga cgaacgagtc aaagcggatg    780
agagcctgac agtccccatg tccccatcga caacacgcaa cgacaaaaag ggggcgggc    840 tcgggcgcgt tatggctggg ttcatcgacc cggggctcac ctgggaagat ctggcctggg    900
tgcgacaaca tacccatctc cccgtttgtc tgaagggaat tatgtccgca gacgatgcca    960
ttctagccat gaaattggga ctagatggca tcctgctctg caaccacggc ggccg         1015
```

<210> SEQ ID NO 3
<211> LENGTH: 1307
<212> TYPE: DNA
<213> ORGANISM: Monascus ruber

<400> SEQUENCE: 3

```
tgggtgggya aytgyaatga rctgaatgct ggttackccg ccgatggcta cgctcgtatc     60
aagggtatct ctgccctgat caccactttc ggtgtcggtg agctctctgc cgccaacgcc    120
atcgccggtt cctactcgga rcgggtgccc gttgtccaca ttgtcggtga gcccagcacg    180
gcatcccaga caaccgcca gcttctgcac cacaccctcg gaaacggtga cttcgatgtc    240
ttcgagaaga tcttcgccaa gatctctact tccgtcgtta agattagaga ccccgccaat    300
gccgccacca tgatcgacca cgttctccgg gaatgtgtta tccagagccg ccccgtctac    360
atcggtctgc cctctgatat ggttaccaag aaggttgagg gagcccgcct gaagaccccc    420
atcgacctgt ccctccccga gaaccccaag gagaaggagg actacgtcgt cagcgtcgtt    480
ctcaagtatc tgcacgctgc caagaacct gtcatcctcg tcgatgccgg tgtcaaccgc    540
cacaatgccc aggctgaggt gcacgagctg atcaagaagt ctggaatccc caccttcatc    600 accccccatgg gcaagggcgg tgttgacgaa accctcccca actacggcgg tgtctacgcc    660
ggtaccggtt ccaacagggg cgtccgcgag cgtgtcgagg aatctgacct catcctgaac    720
atcggacctc tccagtccga cttcaacacc accggcttct cctaccgcac cagccagctc    780
aacaccatcg agttcgaccg cgacagcgtc caggtccgct actcctacta ccccgacatc    840
cagcttaagg gagttctcca gaacctcatc gccaccatgg gcgaactcaa catcgagcct    900
ggcccgaccc cctccaacgc cctccccgcc aacggcgttg accacgaaac tgcagagatc    960
acccacgaat ggctctggcc catggtcggc aactggctcc gcgaaggtga tgttgtcctc   1020
actgaaaccg gtaccgccaa cttcggtatc tgggaaaccc gcttcccaa gaacgttcag   1080 gccatctccc aggtcctctg ggggttccatc ggttactccg tcggtgcctg cttgggtgct   1140
gctctcgccg ctcgggaact tggcgacaac cgtgtcctac tcttcgtcgg tgatggtagc   1200
```

| | | | |
|---|---|---|---|
| ttycagatga | ccgcccagga gatcagcact atgatccgtc agggattgaa gcctattgtc | | 1260 |
| ttcgtcatct | gcaacaacgg ctacacmatc garmgctaca tccacgg | | 1307 |

<210> SEQ ID NO 4
<211> LENGTH: 1287
<212> TYPE: DNA
<213> ORGANISM: Monascus ruber

<400> SEQUENCE: 4

| | | |
|---|---|---|
| ctgaacgccg sctacgccgc cgacggatay gctcgtgtca atggaatcgc tgccttggtt | | 60 |
| actactttcg gtgtaggaga gctgtcagca gtgaacgcca ttgcgggagc ctactcagag | | 120 |
| tatgtaccca tcgttcacat tgttggccaa ccaaatacaa ggtcacagag agatggaatg | | 180 |
| ctgttgcatc atacgttggg caacggcgac tttgatgtct ttaccaagat gagtgcttcc | | 240 |
| atttcgtgcg ctgttgcaaa gttgaacgac ccccatgaag ctgcaacgct catcgaccac | | 300 |
| gccattcggg aatgctggat cgcagcaga ccggtgtaca tcaccctccc tacagacatc | | 360 |
| gtcacgaaga agtcgaagg tgaaaggctg aagaccccaa ttgacctgac aatgccagag | | 420 |
| aatgaagcag aaagggaaga ttacgtggtg gatgttgttt tgaaataccct gcaagccgcg | | 480 |
| aaaaacccag tcattctagt tgacgcatgc gcaatccgtc acgggtcct ggacgaggta | | 540 |
| catgaccttg ttaaggcttc tggcttgcca acctttgtga ccccaatggg caaggagca | | 600 |
| gtggacgaga ctcatccaaa ttatggtggt gtgtatgctg gagatgggtc taataccggc | | 660 |
| gtccgtgaag ttgttgaagc ttccgacctt attctgagca ttggcgccat taaatccgat | | 720 |
| ttcaatactg ccggcttcac ataccgcatc ggccaactta acacgatcga cttccatagt | | 780 |
| accttcgtgc gagtgaggta ttcggagtac ccgaacacaa acatgaaggg tgttctaagg | | 840 |
| aagatcatcc agaaaatggg cccctcagc aagacgccta ttccaaagac tatcaacaag | | 900 |
| gttccagaac atatcaaagc ttctggtgac acgcggatta ctcatgcttg gttgtggccg | | 960 |
| acagtcggac agtggctgca gccggaggat gttgtcgtca ctgagactgg aactgcaaac | | 1020 |
| tttggaatct gggaaaccag gttcccacac ggtgtcacgg ctataagcca agtcctctgg | | 1080 |
| ggaagcattg ggtacacggt tggagcatgt caaggcgccg cactagctgc aaaggagata | | 1140 |
| ggcaaccgtc gcactgtact ttttgttggc gatggcagtt tccagcttac cgcgcaggaa | | 1200 |
| gtgagcacca tgctcagaaa taagctgaac ccgatcattt ttgtgatctg taacgaaggg | | 1260 |
| tayacratcg agcgctacat ccatggc | | 1287 |

<210> SEQ ID NO 5
<211> LENGTH: 1680
<212> TYPE: DNA
<213> ORGANISM: Monascus ruber

<400> SEQUENCE: 5

| | | |
|---|---|---|
| atgaccactg tcggaagcta cctcgcagaa aggctctccc aaattggcat cgagcgccac | | 60 |
| ttcgtcgtcc caggcgacta caacctcatc ctcctcgaca aactccaaca acaccccaaa | | 120 |
| ctcgacgaaa tcaactgcac aaatgaacta aactgctcca tggccgcaga aggctacgcc | | 180 |
| cgcgcaaaag gcgtagccgc ctgcgtcgtg acgttcagcg tcggcgcatt ctccgcattc | | 240 |
| aacggcatcg gcagcgcata cggtgagaat ctccctgtca tcctcatctc cggttcccct | | 300 |
| aataccaacg atcttggctc gtcgcattg ctgcatcata cgatcggtac gcataatttt | | 360 |
| gactaccagc ttgagatggc gaaaaatatc acctgctgtg ctgttgcgat tcgtcgtgcc | | 420 |

-continued

```
tcggatgcgc cgcggttgat cgacgaggct attcgcaccg cacttcgggc gcggaaacca    480
gcgtatattg agattcctac gaacctctcg ggccagccgt gttccctgcc cggaccggcg    540
tcggggattc tcaagccgga tacgagtgat attgatactc ttgcggaagc gctgaaggca    600
gccaacgact tcctctctac ccggaacaag gtgtccttac tggttggccc taaggttcgc    660
gcagcaggcg ctgaacatgc cgtgatccat cttgctcaag ccctgggatg cgcggtggcc    720
gtgctaccca gtgccaaatc gttcttcccg gagactcatc cgcagttcgt gggtgtatac    780
tggggcgaag tgagcacgaa gggcgcgaat gctatcgtcg actggtccga taccttatt    840
tgcgtgggga cggtttacac cgactacagc accgttggat ggacggggct acccgaagca    900
gccagtctga ccattgacct ggaccatgtc agtttccctg gatccgatta caaccagatc    960
catatgctgg agttcgtggc aggactggcg aagctggtga agaagaaccc cctgacactc   1020
gtcgaatata accgtctgca accagaccct ctcgttcaca cgccatctcc gccggatcaa   1080
cgactgagcc ggcgagaaat gcagtaccag atcagccagt tcctgacgcg caacacgacg   1140
gtcgttgtgg acacgggcga ctcgtggttc aacgggatgc agatggacct tccggacgga   1200
gtgagatttg aggttgagat gcaatgggga cacatcggat ggtccgttcc agcagcactg   1260
ggtctggccg ccgcaaaccc cgagcgacag atagtcgtca tggtaggcga tgggtcgttc   1320
cagatgacgg ccacgaggt gtcaaatatg actcgattag gctaccgat tatcatcttc    1380
ctgatcaaca atgacgggta cacaatcgaa gtcgagatcc acgatggcat ctacaacaac   1440
atcaagaact gggattacgg cgcgttcgtc gagtcgttca tgccaagga gggacatggg   1500
aaggggtatc gtgttaccac ggcggggaa atgcacaggg ccattgaggc ggcgaagaag   1560
aataaacagg ggccaacact aatcgagtgt gatattgatc gcgatgattg cagtaaggag   1620
ttgatcagtt gggggcatta tgtggctgct gcgaatggca agcctcctgt tgccaggtga   1680
```

<210> SEQ ID NO 6
<211> LENGTH: 1655
<212> TYPE: DNA
<213> ORGANISM: Monascus ruber

<400> SEQUENCE: 6

```
atgtctcaac ctaagcttac cggcgctgat atcgccaaac acaattccaa ggactcgtgc     60
tgggtcattg tccacgggaa agcatacgat gtcacggact tcctgccagg tattgattga    120
ccccctgtc cgggaattcc gagatgctgc ctgcgttcat tgaatactga tttgcatgaa    180
tttgatcaat atagaacat cccggtggcc agaagattat cctgaagtat gccggcagag    240
atgccacgga agaattcgag cccatccacc ccccggatac cctggacaag tacctcgaca    300
agtcaaagca cttgggcgag gtcgacatgg ccactgtcgc acacgacgag aaggctgtcg    360
atcccgagga gacggctcgc caggaaagaa tcaagctcat gccatcgttg caatcctgct    420
acaatctgat ggactttgaa tccgtggcgc agcaggtcat gaagaagact gcgtgggcat    480
actactcaag tggtgctgat gatgaaatcg tatgaccata tctggatttc tcgttcccttt    540
tgcagcacat actgacttgc gtctgttcac agaccctgcg agaaaccac actgccttcc    600
ataagatctg gttccggccg cgagtcctag tcgacgtgga acatgtcgac tactctacga    660
ccatgctggg aaccaaggtc tccgctccct tctatgtgac ggccacagcc ctgggcaaac    720
tgggacaccc cgagggtgag gtcgttctca cccgttcctc ctaccgtcac aacgtcatcc    780
agatgattcc cacgctcgcc tcgtgctcct ttgacgagat tattgacgcc cgccaaggcg    840
atcaggtcca gtggctgcag ctctacgtca acaagaaccg cgatatcacc aagcgcattg    900
```

```
tgcaacatgc cgaagcccgc ggctgcaagg gcctcttcat caccgtcgac gccccgcaat     960
taggtcgtcg agagaaagac atgcgctcca agttctccga cgagggctcc aacgtccaga    1020
aagaagaggg tgaggagaac gtcgaccgct ctcagggtgc cgcccgtgct atctcctcgt    1080
tcatcgaccc cgccctctcc tggaaggata tcccctggtt ccaatccatc acgaagatgc    1140
ccatcgtcct gaagggtgtg cagtgcgtcg aagacgtttt ccgtgctatc gaagccggag    1200
tccagggtgt tgtgctgtcc aatcacggtg gccgtcagct cgagttcgca ccatcggctg    1260
tcgagcttct ggccgaggtt atgcctgcgc tgcgccagcg cggcttggag aacagcatcg    1320
aggtgtacat cgacggtggc atccgcagag gcactgatat cgtcaaggcg ctctgccttg    1380
gcgcccaggg cgtggggatt ggtcgtcctt tcctgtacgc catgtcggcg tacggccagg    1440
ccggtgtcga caaggccatg cagcttctca aggatgagat ggagatgaac atgagactca    1500
tcggagccac taaggtctcc gagctgagcc ccagcctcgt cgatacccgc ggtcttcttg    1560
gtggtcacca cgctcctgtt ccgtccgaca cgctgggcat gaaggcgtac gatgcgctcc    1620
aggctccgcg gttcaacgaa aagtcgaagt tgtag                              1655
```